(12) United States Patent
Spencer et al.

(10) Patent No.: US 8,855,809 B2
(45) Date of Patent: Oct. 7, 2014

(54) MATERIAL SORTING TECHNOLOGY

(75) Inventors: David B. Spencer, Bedford, MA (US);
Jeffrey J. Webster, Leeds, MA (US);
Aldo M. Reti, Cape Coral, FL (US);
Edward J. Sommer, Jr., Nashville, TN (US); Richard E. Hill, Nashville, TN (US); R. Lynn Conley, Antioch, TN (US)

(73) Assignee: Spectramet, LLC, Bedford, MA (US)

( * ) Notice: Subject to any disclaimer, the term of this patent is extended or adjusted under 35 U.S.C. 154(b) by 94 days.

(21) Appl. No.: 13/600,969

(22) Filed: Aug. 31, 2012

(65) Prior Publication Data

US 2013/0079918 A1    Mar. 28, 2013

Related U.S. Application Data

(60) Provisional application No. 61/530,244, filed on Sep. 1, 2011.

(51) Int. Cl.
| | | |
|---|---|---|
| *G06F 7/00* | (2006.01) | |
| *G01N 23/06* | (2006.01) | |
| *B07C 5/346* | (2006.01) | |
| *G01N 23/02* | (2006.01) | |
| *G01N 23/223* | (2006.01) | |
| *B07C 5/34* | (2006.01) | |

(52) U.S. Cl.
CPC .............. *B07C 5/3416* (2013.01); *G01N 23/06* (2013.01); *B07C 5/346* (2013.01); *G01N 23/02* (2013.01); *G01N 23/223* (2013.01); *G01N 2223/64* (2013.01); *G01N 2223/643* (2013.01)
USPC ........... 700/223; 700/222; 700/218; 700/228; 378/53

(58) Field of Classification Search
None
See application file for complete search history.

(56) References Cited

U.S. PATENT DOCUMENTS

| | | |
|---|---|---|
| 4,848,590 A | 7/1989 | Kelly |
| 6,888,917 B2 | 5/2005 | Sommer, Jr. et al. |
| 7,099,433 B2 | 8/2006 | Sommer et al. |
| 7,430,274 B2 | 9/2008 | Connors et al. |
| 7,564,943 B2 | 7/2009 | Sommer, Jr. et al. |
| 7,763,820 B1 | 7/2010 | Sommer, Jr. et al. |

(Continued)

FOREIGN PATENT DOCUMENTS

| | | |
|---|---|---|
| JP | 2004093511 | 3/2004 |
| WO | WO 02/50521 A2 | 6/2002 |

(Continued)

OTHER PUBLICATIONS

Invitation to Pay Additional Fees with Partial Search Report for International Application No. PCT/2012/053405 mailed Jan. 23, 2013.

(Continued)

*Primary Examiner* — Yolanda Cumbess
(74) *Attorney, Agent, or Firm* — Wolf, Greenfield & Sacks, P.C.

(57) ABSTRACT

Systems for sorting materials, such as those made of metal, are described. The systems may operate by irradiating the materials with x-rays and then detecting fluoresced x-rays, transmitted x-rays, or both. Detection of the fluoresced x-rays may be performed using an x-ray fluorescence detector array. The systems may be configured to provide high throughput sorting of small pieces of materials.

97 Claims, 23 Drawing Sheets

(56) References Cited

U.S. PATENT DOCUMENTS

| | | | |
|---|---|---|---|
| 7,848,484 | B2 | 12/2010 | Sommer, Jr. et al. |
| 8,144,831 | B2 | 3/2012 | Sommer, Jr. et al. |
| 2006/0254679 | A1* | 11/2006 | Odashima et al. ............ 148/551 |
| 2007/0030953 | A1 | 2/2007 | Sommer, Jr. et al. |
| 2009/0236268 | A1 | 9/2009 | Shulman |
| 2010/0017020 | A1 | 1/2010 | Hubbard-Nelson et al. |
| 2010/0111252 | A1* | 5/2010 | Sommer et al. ................. 378/45 |
| 2010/0185319 | A1* | 7/2010 | Petzold et al. ................ 700/223 |
| 2010/0219109 | A1* | 9/2010 | Roos et al. ..................... 209/3.1 |

FOREIGN PATENT DOCUMENTS

| | | |
|---|---|---|
| WO | WO 2008/126892 A1 | 10/2008 |
| WO | WO 2008126892 A1 * | 10/2008 |
| WO | WO 2011/159269 | 12/2011 |

OTHER PUBLICATIONS

Sitko, R., "Quantitative X-Ray Fluorescence Analysis of Samples of Less than 'Infinite Thickness': Difficulties and Possibilities," *Psectrochimica Acta Part B Atomic Spectroscopy* 64(11-12):1161-1172 (2009).

International Search Report for International Application No. PCT/US2012/053405 mailed Mar. 18, 2013.

Written Opinion for International Application No. PCT/US2012/053405 mailed Mar. 18, 2013.

\* cited by examiner

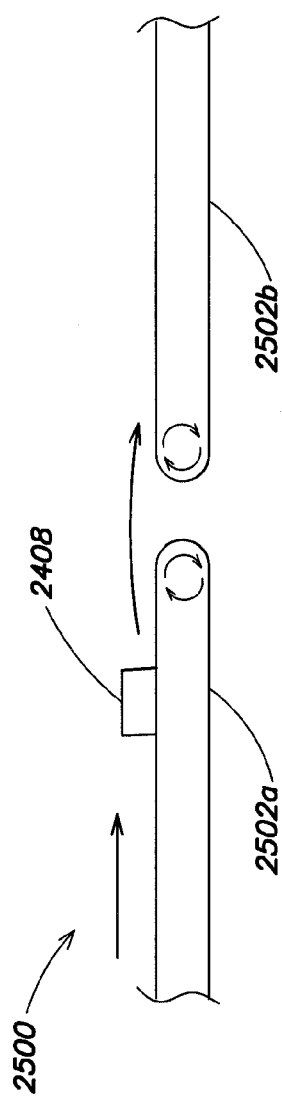
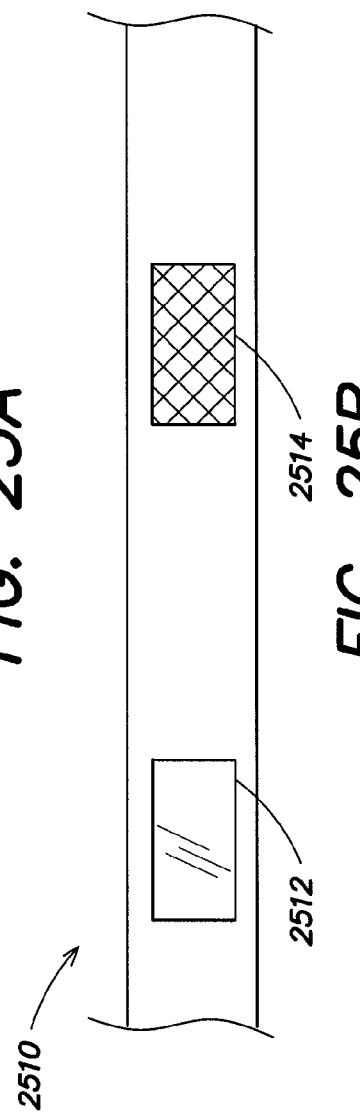
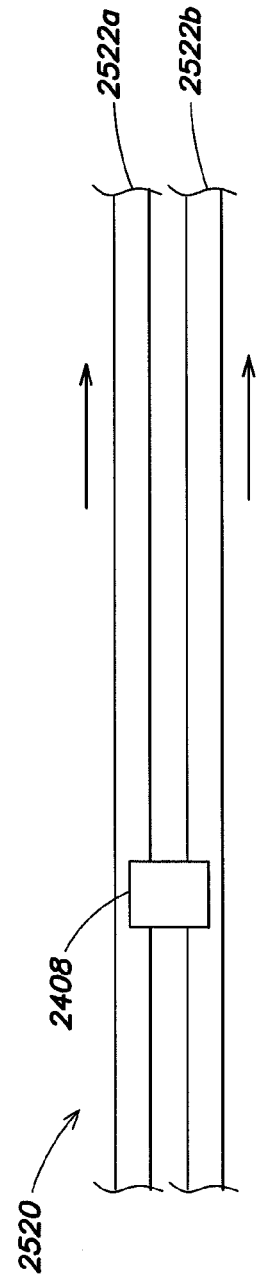

MATERIAL SORTING TECHNOLOGY

CROSS-REFERENCE TO RELATED APPLICATIONS

The present application claims the benefit under 35 U.S.C. 119(e) of U.S. Provisional Patent Application Ser. No. 61/530,244 filed on Sep. 1, 2011 and entitled "Metal Sorting Technology," which is incorporated herein by reference in its entirety.

BACKGROUND

1. Field

The technology described herein relates to materials sortation, and related apparatus and methods.

2. Related Art

Various manufacturing and scrap processes produce small pieces of metal. For instance, as superalloy for instance as nickel or cobalt based superalloy components are processed, a tremendous amount of machine turnings are generated, such as those shown in FIG. 1. After they have been shredded, processed to remove lubricants, and dried, they are known as clean superalloy machining chips, as shown in FIG. 2.

The large number of superalloy products manufactured by the industry requires the production of a vast range of metal alloys having various compositions. The resulting wide range of alloys and scrap materials from different end user applications are returned to scrap processors for recycling and reuse. A scrap has its greatest value when it is returned to the same alloy as when originally produced, in a clean and dry condition. If a mixture of alloys can be sorted or graded into its original alloy composition, its value will increase. Absent removal of contamination via a cost effective mechanism, the value of this scrap can be worth far less than its potential value.

The value added depends upon the value of the mixed scrap and the competitive costs for producing high-grade specification alloys from scrap versus from primary virgin sources. Today, the most common automated methods for sorting scrap into grades or types at a scrap yard are: shredding or shearing, magnetic separation, eddy current separation, and heavy media separation. Some equipment purports to automatically sort metal alloys using color sensors. In most instances for sorting of typical nonferrous metal scrap, human visual recognition is the primary means for sorting one grade of scrap from another.

Handheld and bench top x-ray fluorescence (XRF) sorters are available for assisting operators in sorting superalloys. Even though this method takes several seconds per item, with superalloy scrap being so valuable, even in the U.S., this method of scrap sorting can be cost effective on large items of scrap. However, the current handheld and bench top XRF sorting technologies in existence today are not cost effective on small items of scrap such as those shown in FIG. 2. They are, therefore, also hopelessly incapable of cost effectively sorting individual machining chips of the type shown in FIG. 3, since such machining chips are even smaller than the items of FIG. 2.

Commercially efficient sortation of small pieces of metal has yet to be developed.

SUMMARY

According to an aspect of the present technology, a material sorting system is provided, comprising a conveyor configured to convey pieces of material, and an x-ray source configured to irradiate the pieces of material with incident x-rays as they are conveyed by the conveyor to generate fluoresced x-rays from the pieces of material and transmitted x-rays transmitted through the pieces of material. The system further comprises an x-ray fluorescence detector array configured to detect the fluoresced x-rays and produce x-ray fluorescence data and an x-ray transmission detector configured to detect the transmitted x-rays and produce x-ray transmission data.

According to an aspect of the technology, a method of sorting material is provided, comprising conveying pieces of material with a conveyor, and irradiating the pieces of material with incident x-rays as they are conveyed by the conveyor to generate fluoresced x-rays from the pieces of material and transmitted x-rays transmitted through the pieces of material. The method further comprises detecting the fluoresced x-rays with an x-ray fluorescence detector array and producing x-ray fluorescence data with the x-ray fluorescence detector array and detecting the transmitted x-rays with an x-ray transmission detector and producing x-ray transmission data with the x-ray transmission detector.

According to an aspect of the technology, a system is provided, comprising an x-ray source configured to irradiate a stream of pieces of material, and a multi-channel x-ray fluorescence detector array configured to detect x-rays fluoresced by the pieces of material. The system further comprises collimation hardware configured to collimate fluoresced x-rays from the stream of pieces of material on the multi-channel x-ray fluorescence detector array.

According to an aspect of the technology, a method of separating pieces of material is provided, comprising irradiating the pieces of material with incident x-rays using an x-ray source, detecting transmitted x-rays transmitted through the pieces of material to produce x-ray transmission data, and analyzing the x-ray transmission data to detect an absorption edge corresponding to an energy level for an element of interest and to determine whether a discontinuity in the x-ray transmission data exists approximately at the absorption edge.

BRIEF DESCRIPTION OF THE DRAWINGS

Various aspects and embodiments of the technology will be described with reference to the following figures. It should be appreciated that the figures are not necessarily drawn to scale. Items appearing in multiple figures are indicated by the same reference number in all the figures in which they appear.

FIGS. 25A-25C illustrate non-limiting examples of conveyor configurations.

DETAILED DESCRIPTION

Figure 1:
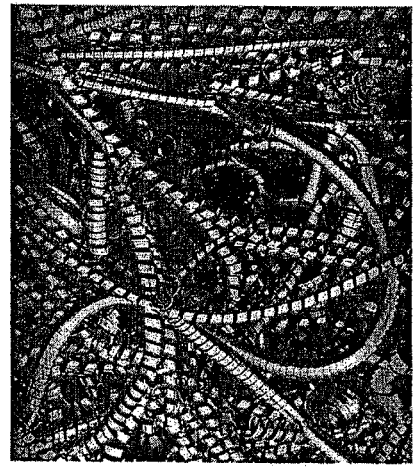
FIG. 1 illustrates machine turnings resulting from processing of superalloys.

In view of the foregoing, various aspects are described herein providing apparatus and methods for materials sorting. According to some aspects, high speed, high volume sorting of small pieces (e.g., chips, cobbles, and other small pieces) of materials (e.g., metals) is provided, but it should be clear that the methods and apparatus are also applicable to other types and forms of matter. Systems are described for providing such sorting functionality in an automated manner, thus increasing throughput and ease of use.

For simplicity, the following description focuses on analysis and sortation of metals. However, not all aspects are limited to working with metals. One or more aspects may apply to glasses, mineral ores, or other materials.

According to an aspect, sorting of metal pieces involves irradiating the metal pieces with incident (source) x-rays. The resultant x-rays emitted from a piece (fluoresced, scattered, transmitted, etc.) may be detected and analyzed. The pieces may then be sorted.

According to an aspect of the present technology, an x-ray sorting system utilizing x-ray fluorescence and x-ray transmission is provided. The system comprises a conveyor configured to convey pieces of material, an x-ray source configured to irradiate the pieces of material with incident x-rays as they are conveyed by the conveyor to generate x-rays fluoresced from the pieces of material and x-rays transmitted through the pieces of material, an x-ray fluorescence detector array configured to detect the fluoresced x-rays and produce x-ray fluorescence data, and an x-ray transmission detector configured to detect the transmitted x-rays and produce x-ray transmission data.

In an embodiment, the system further comprises a processor configured to: receive the x-ray fluorescence data and the x-ray transmission data, and determine thickness data based at least in part on the x-ray transmission data, and combine the thickness data with the x-ray fluorescence data to determine at least a partial composition of one or more of the pieces of material.

In an embodiment, the x-ray transmission data comprises data about two or more energy levels, and the processor may be configured to determine the thickness data at least in part by comparison of the x-ray transmission data of the two or more energy levels. The x-ray fluorescence detector array may comprise an array of x-ray fluorescence detectors configured to detect fluoresced x-rays fluoresced from pieces of material disposed on different parts of the conveyor. In an embodiment, the array of x-ray fluorescence detectors is arranged substantially across a width of the conveyor.

In an embodiment, the x-ray transmission data comprises data about a single energy level. The value corresponding to the single energy level may be integrated over a narrow energy range (e.g., e.g., 30 keV+/−100 eV), though are techniques are also possible. The transmission data relating to a single energy level may be processed in combination with XRF data in some such embodiments.

According to an embodiment, the x-ray transmission detector comprises at least one row of multi pixel x-ray transmission detectors positioned approximately transverse to, ideally perpendicular to, the material flow or conveyor flow direction. The x-ray transmission detector array may comprise two rows of x-ray transmission detectors designed to detect x-rays at different energy levels.

The conveyor of the system may include one or more openings so that x-rays, either incident or resultant x-rays, particularly lower energy x-rays can be emitted by the source onto the pieces and/or detected from the pieces while conveyed without being absorbed by the conveyor materials or picking up extraneous x-ray signals emitted from the conveyor itself. To further increase signal to noise ratios the open volume may be filled with air or other atmosphere (helium), or held under vacuum. The conveyor may comprise one or more mesh sections or may be covered with relatively x-ray "transparent" materials (low x-ray absorption thin polymers, as one example). In an embodiment, two conveyors are configured in parallel with a gap there between, such gap being filled with x-ray "transparent" materials or open mesh. The open gap between the parallel conveyors may be covered with x-ray transparent material so pieces do not fall through the gap, but that also do not emit x-rays in the energy range of the pieces in order to reduce extraneous noise. In an alternative, the two conveyors are configured in series. In an embodiment, the conveyor comprises two conveyors configured to convey the material into and out of an irradiation zone in which the x-ray source is configured to irradiate the pieces of material with the incident x-rays while "jumping a gap" between the two conveyors where one conveyor is slightly at lower elevation than the other in the vertical plane. In an embodiment, the conveyor comprises a vibrating feeder or slide.

In an embodiment, the x-ray fluorescence data and/or x-ray transmission data form a spectrum. The system may comprise a processor configured to process the spectrum. The processor may be configured to perform resultant vector analysis of the spectrum and/or decision tree processing in an embodiment. In an embodiment, the processor comprises a first partition dedicated to processing the x-ray fluorescence data and x-ray transmission data.

For instance, the processor may form at least part of a sorting computer with hard real-time processing capability. The computer includes an isolated partition dedicated to the sorting task, which preferably (and in some cases, must) execute within guaranteed timing and latency constraints, and another partition that does system configuration and user interface. The computer software architecture may exhibit independence of the two partitions so that system configuration and user interface actions cannot delay or suspend the real-time sorting functions. This may be accomplished by the primary computer processing all data for all channels simultaneously, or alternatively, by adding dedicated processors for each channel which calculate rapidly in real time and feed processed data to the central computer for integration with other data and information associated with the operation.

In an embodiment, the sorting system is configured to separate titanium alloys from superalloys. In an embodiment, the x-ray fluorescence detector array is configured at approximately 45 degrees from a direction at which the x-ray source irradiates the pieces of material to reduce the detection of scattered and incident x-rays being captured by the sensor. In some embodiments, the superalloys may be nickel or cobalt based superalloys, though not all embodiments are limited in this respect. In yet another embodiment, the sorting system is configured to separate superalloys from titanium alloys.

In an embodiment, the pieces of material in the form of chips have thicknesses up to approximately 5 mm, or even more as in the case of cobbles, and even more for pieces of scrap metal.

In an embodiment, the system further comprises an ejector configured to selectively direct the pieces of material off the conveying device into a capture or storage device after they are irradiated with the incident x-rays. The ejector may comprise an air ejector. The ejector may comprise a paddle ejector in some embodiments.

In an embodiment, the x-ray transmission detectors and/or detector array and/or x-ray fluorescence detectors and or detector array comprises one or more detectors selected from the group consisting of: Cadmium Telluride (CdT), Cadmium Zinc Telluride (CZT), Lithium-drifted silicon (SiLi) and Silicon Drift (SDD) detectors. In an embodiment, the x-ray transmission detector is configured to produce an x-ray image (x-ray line scan camera image) of at least one piece of the pieces of material. In an alternative embodiment, one or more detectors of one or more detector types may be used (for detecting x-ray fluorescence, x-ray transmission, or both). Alternatively, phosphor-on-silicon detectors may be used in some embodiments.

In an embodiment, the material sorting system is configured to sort the pieces of material based at least in part on the effective Z (Zeff) of the pieces using the x-ray transmission data (e.g., corresponding to two or more energy levels in some embodiments). In an embodiment, the pieces of material comprise metal alloys comprised of more than one element (alloys) and wherein the material sorting system is configured to sort the alloys. In an embodiment, the pieces of material comprise glass and/or ceramic, and wherein the material sorting system is configured to sort the glass and/or ceramic. In an embodiment, the pieces of material comprise mineral ores and wherein the material sorting system is configured to sort the mineral ores.

As described above, in some embodiments sorting of materials is provided in a fully automated manner. In some embodiments, the system further comprises a processor configured to process the x-ray transmission data to determine a volume of at least one of the pieces of material. The system may comprise a processor configured to process the x-ray transmission data to produce an image and to determine attenuation, and thus estimate thickness. This is particularly useful for metals that are bent and twisted or balled up such that an optical sensor cannot determine thickness of the metal.

According to an aspect of the technology, a method of sorting materials is provided. The method may involve irradiating the materials with x-rays and detecting the resulting x-rays (fluoresced, scattered, and/or transmitted). The method may be used in connection with systems of the types described above.

According to an aspect of the technology, a method of sorting material is provided, comprising conveying pieces of material with a conveyor, irradiating the pieces of material with incident x-rays as they are conveyed by the conveyor to generate x-rays fluoresced from the pieces of material and x-rays transmitted through the pieces of material, detecting the fluoresced x-rays with an x-ray fluorescence detector array and producing x-ray fluorescence data with the x-ray fluorescence detector array, and detecting the transmitted x-rays with an x-ray transmission detector and producing x-ray transmission data with the x-ray transmission detector.

The method may further comprise: receiving the x-ray fluorescence data and the x-ray transmission data with a processor; determining thickness data with the processor based at least in part on the x-ray transmission data; and combining the thickness data with the x-ray fluorescence data with the processor to determine at least a partial composition of one or more of the pieces of material. In an embodiment, the x-ray transmission data comprises data about two or more energy levels, and the processor determines the thickness data at least in part by comparing the x-ray transmission data of the two or more energy levels. According to one embodiment, both XRF and x-ray transmission data are used (simultaneously, or converging iteratively) to determine composition and thickness of a piece of material.

In an embodiment, the x-ray fluorescence detector array comprises an array of x-ray fluorescence detectors configured to detect fluoresced x-rays fluoresced from pieces of material disposed on different parts of the conveyor. The array of x-ray fluorescence detectors may be arranged substantially across a width of the conveyor.

In an embodiment, the x-ray transmission detector is a single array of small x-ray transmission detectors. In an embodiment, the x-ray fluorescence detector array comprises two rows of x-ray fluorescence detector arrays which may be either stacked on top of each other in a single line or row or in two rows adjacent to each other and perpendicular to material flow. When detector arrays are stacked, the detectors of the two arrays may be the same type as each other or different types. In another embodiment a series of single detectors, for example Amptek Si-Pin or SDD detectors with sensors up to 25 mm each, may be arranged side by side or in a staggered line to effectively form an array or line scan "camera" having an effective "pixel" size of one quarter inch, more or less.

The conveyor may be any suitable type of conveyor, including any of those previously described herein, such as those including one or more gaps, multiple conveyors in series or parallel, mesh conveyors, or any other suitable type of conveyor. In some embodiments, the conveyor may be a vibrating feeder or inclined ramp which the material slides down.

In some embodiments, irradiating the pieces of material with x-rays may result in the x-ray fluorescence data and/or x-ray transmission data representing a spectrum. The method may comprise processing such spectra with a processor, which may be any suitable processor (e.g., a general purpose processor, dedicated hardware, etc.). Processing the spectrum may comprise performing resultant vector analysis of the spectrum and/or decision tree processing.

The methods described herein may be used to sort and separate various types of material. In an embodiment, the method is used to separate titanium alloys from superalloys.

In an embodiment, the method may use an x-ray fluorescence detector array that is configured at approximately 45 degrees from a direction at which the x-ray source irradiates the pieces of material. In an embodiment, the pieces of material when in the form of chips have thicknesses up to approximately 5 mm, or much more in the cases of cobbles and small chunks of scrap pieces.

The method may comprise selectively ejecting the pieces of material after they are irradiated with the incident x-rays. Selectively ejecting the pieces of material may comprise using an air ejector. Selectively ejecting the pieces of material may comprise using a paddle ejector.

The method may use various types of x-ray detectors. According to an embodiment, the x-ray transmission detector and/or x-ray fluorescence detector array comprises one or more detectors selected from the group consisting of: Cadmium Telluride (CdT), Cadmium Zinc Telluride (CZT), SiLi and Silicon Drift (SDD) detectors.

The method may comprise producing an x-ray image of at least one piece of the pieces of material using the x-ray transmission data effectively acting as a x-ray line scan camera. The method may be used to sort the pieces of material based at least in part on the effective Z (Zeff) of the pieces using the x-ray transmission data. The pieces of material may comprise alloys and wherein the method is used to sort the alloys. In an embodiment, the pieces of material comprise glass which term (glass) is also intended to include herein the types of matter customarily known as ceramics, metal oxides, metal sulfides and metal chlorides, and the method is used to sort the glass. In an embodiment, the pieces of material comprise mineral ores and the method is used to sort the mineral ores.

In an embodiment, the method is fully automated. However, not all embodiments are limited in this respect.

In an embodiment, the method further comprises determining a volume of at least one of the pieces of material using the x-ray transmission data. The determined volume may be used, for example, in determination of what the type of material is and/or how to sort the material.

According to an aspect of the present technology, an x-ray system is provided which utilizes x-ray detectors in a line-scan configuration. According to an embodiment, a system comprises an x-ray source configured to irradiate a stream of pieces of material, and a multi-channel x-ray fluorescence detector array configured to detect x-rays fluoresced by the pieces of material, and collimation hardware configured to collimate fluoresced x-rays from the stream of pieces of material on the multi-channel x-ray fluorescence detector array.

In an embodiment, the x-ray fluorescence detector array comprises energy dispersive x-ray detectors. The system may further comprise a conveyor configured to convey the stream of pieces of material in two or more parallel channels. The conveyor may be any of the types previously described herein or any other suitable type.

It should be appreciated that the term "channel" is used herein in different contexts. Note that the channels may be "imaginary" in terms of channels on the conveyor belt since the material may still be randomly distributed on the belt and yet when flowing in a given direction forms an imaginary channel because the pieces are not moving on the belt and in effect are moving down imaginary channels having a width equal to the piece width across the belt. In other cases, the conveyor belt may actually have physical, slides, chutes or channels that contain the materials constraining them to fall within real channels on the conveying device. In one context, "channel" refers to the physical placement of pieces of material (e.g., on a conveyor). For example, the pieces may be conveyed in channels. In a second context, multi-channel detectors and arrays may be used for material placed randomly on the conveying device. Thus, the meaning of the term will depend on the context in which it is used.

In an embodiment, the multi-channel x-ray fluorescence detector array comprises a plurality of detectors, at least one of which is configured to produce x-ray fluorescence data representing an x-ray fluorescence spectrum. In an embodiment, each x-ray fluorescence detector of the x-ray fluorescence detector array is configured to produce x-ray fluorescence data representing a respective x-ray fluorescence spectrum. The system may further comprise a processor configured to receive the x-ray fluorescence data and concatenate the x-ray fluorescence spectra from the x-ray fluorescence detectors.

In an embodiment, the multi-channel x-ray fluorescence detector array is configured at an angle with respect to a direction at which the x-ray source is configured to irradiate the stream of pieces of material. The angle may be approximately 45 degrees or any other suitable angle.

In an embodiment, the x-ray fluorescence detector array comprises a 24 pixel line scan camera. The arrays of pixels may provide, in some non-limiting embodiments, a resolution between approximately 0.125 inches and 0.375 inches. The pixels may be spread over any suitable distance. In an embodiment, the system further comprises a processor configured to detect x-ray fluorescence data produced by the x-ray fluorescence detector array and to process the x-ray fluorescence data to identify individual pieces of material from the stream of pieces of material.

In an embodiment, the system further comprises a channelized gravity-fed slider configured to present the stream of pieces of material to the x-ray source. In an embodiment, the system further comprises an x-ray transmission detector array configured on an opposing side of the stream of pieces of material from that of the x-ray source.

An absorption edge, absorption discontinuity or absorption limit is a sharp discontinuity in the absorption spectrum of a substance. These discontinuities occur at wavelengths where the energy of an absorbed photon corresponds to an electronic transition or ionization potential. When the quantum energy of the incident radiation becomes smaller than the work required to eject an electron from one or other quantum states in the constituent absorbing atom the incident radiation ceases to be absorbed by that state. For example, incident radiation on an atom of a wavelength that has a corresponding energy just below the binding energy of the K shell electron in that atom cannot eject the K shell electron. According to an aspect of the technology, methods for sorting materials are provided which involve analyzing an absorption edge and making a sorting decision based at least in part on a detected absorption edge. According to an embodiment, a method of separating materials based on absorption edge is provided, comprising irradiating the pieces of material with incident x-rays using an x-ray source, detecting transmitted x-rays transmitted through the pieces of material to produce x-ray transmission data, and analyzing the x-ray transmission data to detect an absorption edge corresponding to an energy level for an element of interest and to determine whether a discontinuity in the x-ray transmission data exists approximately at the absorption edge.

Various types of materials may be sorted using absorption edge processing. In an embodiment, the element of interest is tin, and the method is used to separate tin-bearing titanium alloys from non-tin-bearing titanium alloys.

According to an aspect of the present technology, an x-ray detector having a small pitch level is used in sorting materials of interest irradiated with x-rays. The x-ray detector may be a NEXIS system, and may be suitable for detection of x-ray fluorescence. It should be appreciated that a NEXIS system is a non-limiting example of a suitable detector type, and that other detectors may alternatively be used according to the various aspects described herein. In all those embodiments herein in which the use of a NEXIS detector is described, it should be appreciated that alternative detectors providing the same or similar functionality may be used as well.

According to an aspect of the present technology, a method of using an x-ray detector as a line scan camera is described. A pixelated XRF system (e.g., a NEXIS system or Amptek system, as described further below), may be used as a line scan camera to obtain image data, among other things.

According to an aspect of the present technology, a method of sorting materials comprises using absorption edges with transmission x-ray data to detect and, in some embodiment, identify contaminants that might be present in very small concentrations in the materials of interest.

According to an aspect of the present application, an integrated system is provided that simultaneously collects imaging information, XRF information, and x-ray transmission information. The system may, in some embodiments, obtain from at least some of that information on particle thicknesses that allow for determination of, among things, volumetric or density throughput of a sorting system.

In an embodiment, the system obtains data sufficient for imaging from XRF and x-ray transmission detectors, without optical light imaging sensors.

According to an aspect of the present technology, systems and methods are described for sorting small pieces of material (such as metal) using x-ray techniques. Due to the small size, low x-ray count rates may be all that is available in some embodiments, and x-ray transmission through the pieces of material may be a reality to be addressed. In some embodiments, dual-energy (or multiple-energy) processing is used to determine the thicknesses of the materials, which in turn may be used to normalize x-ray data in sorting the materials. In an embodiment, x-ray transmission data is used to determine particle thicknesses, which in turn are used to normalize collected XRF data.

According to an aspect of the present application, a sortation system comprises two or more x-ray detectors (e.g., a NEXIS system and an Amptek detector). One detector may provide higher spatial resolution, while the other may provide higher spectral resolution. One detector may be configured to detect x-rays energies associated with elements having high Z values (e.g., above 30 keV), while the other may detect a wider range of energies.

In an embodiment, one or both of the detectors may provide multiple energy level detection. For example, one detector may detect up to five energy levels. Data from such a detector may be preferable to data from single-energy or dual-energy detectors in that data corresponding to more than two energy levels may allow for constructing a curve from the resulting data rather than a straight line. Such a curve may be beneficial in identifying materials and therefore in sorting of materials.

According to an aspect of the present technology, a sorting system is provided which allows for high speed sorting of multiple "channels" of particles conveyed on a conveyor in parallel or substantially parallel. In this context, a "channel" refers to spatial positioning of particles on the conveyor, and may be parallel to the direction of travel of the conveyor much like lanes on a highway. The ability to sort from multiple channels of material simultaneously may allow for commercially feasible, high throughput sorting systems. The number of channels may correspond to a number of detectors configured across the conveyor and monitoring respective channels of particles. A stream of particles may comprise multiple channels of particles (much like a highway comprises multiple lanes of traffic).

According to an aspect of the present application, a processing system is provided where the acquisition of x-ray information is performed using a detector, such as a XR-100T-CZT model detector from Amptek, a CZT-based NEXIS detector module from Nova R&D, and a 480 W Monoblock x-ray system from Spellman. A monochromatic source of x-rays may also be utilized in some embodiments. Examples include substitution of a polychromatic source such as an X-ray Tube with a high energy isotope such as Americium. Further, a broad band source can be monochromated by use of a device such as the doubly curved crystal (DCC) such as made by X-Ray Optical Systems, XOS). The Amptek detector may be a single "pixel" device which records an x-ray spectrum as a histogram of x-ray events occurring within 1024 energy bins. The NEXIS (N-Energy X-ray Image Scanning) module may comprise or consist of 256 detectors which are physically arranged as 2 rows of 128 "pixels" with a 1 mm detector pitch. In an alternative embodiment, a single row of detectors may be used and may provide sufficient data for sorting applications. Each column can produce a 128-by-N image, where N is an arbitrary number of frames. The supporting electronics for each of the 256 detectors can resolve $10^6$ (1,000 k) counts per second, for five energy bins.

In an embodiment, the NEXIS system provides a multi-energy x-ray transmission image with high spatial resolution and at a high flux. This can also be accomplished with a series of Amptek CdT or CZT detectors but with current technology the "pixel" spacing would be on the order of ¼ inch (and smaller as technology develops or larger for sorting larger pieces) providing more bins and higher count rates.

According to an embodiment, an enclosure may be included to house the Monoblock x-ray system and the detectors. Within the enclosure a conveying belt or device or vibrating feeder or multichannel ramp or conveyor may transition samples through the detector's field-of-view to record the x-ray transmission characteristics of those samples.

In an embodiment, the acquired spectra may then be processed by MatLab and/or other suitable software and/or fully automated algorithms to produce an analysis and identification of the material including algorithms for closest match resultant vector, decision tree, and others. If shape or thickness is also a factor in the sort, or for included particles such as W, or WC, the NEXIS transmission detector can provide a two dimensional image and thickness information which can be used as information used in the sort.

According to an aspect of the present technology, a method is provided to separate chips of titanium alloys from those of superalloys by comparing their x-ray scattering properties at various energy regions. In one non-limiting embodiment, by examining the spectrum from chips (i.e., the x-ray fluorescence spectrum) acquired at a 45° angle from direct transmission, the x-ray fluorescent peaks from the various constituents are revealed (although superimposed on a background of scattered x-rays). The peaks in this "off-angle" XRF spectrum permit clean separation of the material into its constituent elements or alloy.

In an embodiment, the method allows acquisition of x-ray fluorescence spectral information from small particles to differentiate materials that are close on the periodic table even when the pieces are very small and have thin cross sections, such as aerospace alloy turnings. In an embodiment, the method is also applicable to aerospace scrap material known as "cobbles". Cobbles are pieces of material several times larger than chips, with a typical thickness range of between 1 mm and 15 mm in one embodiment.

Moreover, the method is also applicable to sorting small pieces of metal from the Zebra (Zebra is defined as the scrap metal fraction from automobile shredders having apparent densities typically greater than aluminum. The fraction of automobile shredder metals with densities typical for aluminum and less dense metals such as magnesium is called Twitch. The combination of Twitch and Zebra is defined as Zorba) fraction in non-ferrous concentrates from automotive shredders. This material is generally at least as thick as cobbles. For successful sortation of the Zebra components, the off-angle spectra reveals the XRF peaks of iron, copper and zinc among other elements, thus allowing identification of the various metals, materials and alloys in the Zebra fraction.

According to an aspect of the technology, a method is provided to separate chips as well as other small particulates relying on characterization of an alloy from its transmission spectrum. The method is applicable to separate titanium alloys, particularly, the separation of tin-bearing titanium alloys from those containing no tin. Separation may be based on an examination of the transmission spectrum around the x-ray absorption edge of tin (29.2 keV). If a discontinuity exists, tin is present in the alloy. The method may also be used for other elements than tin and most easily with higher Z elements.

According to an embodiment, the method is also applicable to separate alloys based on the Zeff. The Zeff of an alloy quantifies its absorbance relative to elements and facilitates the separation of high-Z alloys from low-Z alloys. This method is utilized to separate Twitch from Zebra.

According to an aspect of the present technology, a hybrid sorting system is provided, which may include one or more of the following detectors: Cadmium Telluride (CdT), Cadmium Zinc Telluride (CZT), SiLi and Silicon Drift (SDD) detectors. The system may employ transmission data for sortation between materials with a larger difference in Zeff or for detecting inclusions and off-axis XRF data for "fine" sortation between materials with small changes in metal concentrations.

According to an embodiment, the hybrid system comprises a NEXIS detector to produce an "x-ray image" of the sample showing items such as holes or inclusions or surface coatings having different x-ray absorption characteristics, thus allowing sortation to also be conducted based on analysis of these x-ray images as well as based on transmission and XRF data collected.

According to an embodiment, the hybrid system allows for optimal use of CdT and CZT detectors in combination with SDD and SiLi detectors. The hybrid system may include both identification and sortation capabilities suitable for commercial scale operations. According to one embodiment, simultaneously and with the same hardware, the information output is enhanced to include imaging information.

According to an aspect of the present technology, the system and techniques described herein may be applied to alloys utilized in the aerospace industry and in the recycling of automotive-shredder scrap for effective sortation. The system and techniques are also applicable to sortation of mineral ores, glass, and many other materials as well.

According to an embodiment, a system is provided for detection and sortation of deleterious contaminants such as tin-bearing titanium alloys containing about 2% tin and very small tungsten inclusions or particles within a matrix of titanium chips. In an embodiment, a system is provided for detection and sortation of small tungsten inclusions within a matrix of titanium chips at high speeds within a fully automated process.

In an embodiment, a system is provided for detection and sortation of inclusions of small Refractory Metals such as molybdenum (Mo), tantalum (Ta) and others within a matrix of titanium chips at high speeds within a fully automated process. These Refractory Metals may be sorted notwithstanding the fact that they are present, for example, as sulfides or oxides. In some embodiments, the systems and methods described herein may be used to sort metal oxides, sulfides and chlorides.

According to an aspect of the present technology, a high-speed and high-volume system for the sortation of titanium and superalloy machining chips is provided with the primary function to separate a stream of chips according to a desired grouping of alloys, for example separation of a titanium group of alloys from a superalloy (nickel-cobalt based) group of alloys and with a secondary function to purify the stream through removal of any commingled contaminant chips. In the context of some embodiments described herein, "commingled" refers to an intimate mechanically combined mixture of chips having different chemical compositions. As one example, a mixture of superalloy chips and titanium chips blended together may be considered commingled. As another example, pieces of metal containing tungsten carbide bits and those that do not—wherein each chip or piece is mechanically separable from the others because they are not welded together or alloyed together, may be considered commingled. The system may comprise one or more of the following: a mechanism to appropriately distribute and convey a stream of metal chips for presentation to a multi-channel XRF detection array (i.e., XRF line scan camera); an optimal sensing configuration for measuring energy dispersive XRF spectra from metal chips in real-time as they transition a multi-channel (defined herein as simultaneously having parallel material flow down many parallel channels, each containing its own detection sensor) detection area at rates required for commercial sortation. The materials may be randomly dispersed across a conveying device provided the chip size is large compared to the sensor spacing, thereby avoiding the need for physical channeling on the conveying device.

According to an embodiment, a sorting unit is provided comprising or consisting of a presentation mechanism, a multichannel array of energy dispersive XRF detectors (i.e., direct energy detectors in some embodiments) (XRF line scan camera) and real-time data acquisition hardware, utilizing real-time computer analyses of the XRF data to effect a precise pneumatic ejection of selected chips from a stream.

In an embodiment, a system comprises an XRF sensor array and interface hardware designed to transfer the data from an array of detectors to the sorting computer at high speed using one or a plurality of the available single-pixel detectors.

In an embodiment, a XRF sensor array is provided possessing a collimation scheme designed to reduce the "bleed-over" of XRF photons from one detector to the next. The detector array may be positioned "off-axis" from the x-ray sheet so to not interact with source x-rays.

According to an aspect, a method is provided which correlates XRF measurements with chip thickness, obtained from measurements of x-ray attenuation upon passing through a chip, to dynamically adjust peak ratios according to chip thickness. Note that in some sorts where we simply seek to identify the presence of an element that does not belong to what we are trying to produce, we do not need to do a full analysis but simply determine the presence of "off specification" elements which can be done by simply detecting presence at levels above background which may not require as many counts and can be done faster and without normalization and peak ratio analysis. According to an embodiment, such a sorting process utilizes smart data addition where we only need to know bad items are present and not the exact or approximate percentage analysis.

According to an aspect of the present technology, a system is provided including a high-speed x-ray line-scan camera composed from a linear array of x-ray detectors, with each detector, or "pixel", providing an x-ray spectrum by acquiring the energy distribution of fluoresced photons impinging on that detector and where concatenation of these spectra results in a "scan-line" of spectra. A high-speed digital communication interface transfers each scan-line to the sorting computer at approximately 500 scans per second or faster. A sorting computer assembles successive scans into a two dimensional image, and then operates on that image to make the material sortation decisions such as detection of tungsten carbide inclusions in a piece of material. The camera has an image acquisition rate at least on the order of 480 Hz with each image comprising an energy distribution spectrum from each pixel. Thus, a line-scan camera system may comprise 120 pixels (for a 30 inch belt at 0.25 inch detector spacing) where each pixel generates a 512 bin energy distribution histogram of 16-bit energy values. In this case, the data rate from the camera is 120×512×16 bits (or 960 Kbits) every 2.08 millisecond (ms) for an aggregate of 450 Mbits per second.

As new technology evolves, and the sensor art improves, these pixel sizes may reduce and scan rates increase and bin numbers increase along with increasing count rates and energy sensitivity and resolution.

In an embodiment, a system is provided comprising a 24 pixel XRF line scan camera having approximately six inch sensing width for a sortation system.

According to an aspect, a system is provided comprising a material presentation system that may be either a flat belt or a group of channelized gravity-fed sliders, where the material particles are preferably presented to the detectors in a non-overlapping single-layer manner. Alternatively, software that eliminates the edge effects in a non-channelized system allowing sufficiently accurate analysis of individual chips that overlap into the region of adjacent sensors may be utilized.

According to an aspect of the technology, a system is provided that includes an array of closely-spaced x-ray detectors positioned or aligned perpendicular to the material flow and off-axis to the x-ray beam sheet. Thus, x-rays emanating from the x-ray source do not interact with the detectors. The array of detectors functions as an x-ray line-scan camera by acquiring an energy distribution histogram for each pixel in the detector array as x-rays fluoresce from irradiated alloy turning chips passing through the source x-ray sheet beam. An updated set of histograms, or spectra, are transferred to the sorting computer for each scan-line of the acquisition process. Each detector element in the array is shielded by collimation such that only XRF photons from samples directly "beneath" that detector are accepted. X-ray photons from other regions, especially from neighboring pixel areas, are blocked with collimators. A fine pitch x-ray transmission array may be positioned underneath the feed stream of materials to estimate chip thickness from x-ray attenuation and for detection of small dense inclusions which may be too small to produce sufficient x-ray fluorescence flux to be measurable by the XRF line scan camera.

According to an aspect, a system is provided comprising sorting computer with hard real-time processing capability. The computer includes an isolated partition dedicated to the sorting task, which preferably (and in some cases, must) execute within guaranteed timing and latency constraints, and another partition that does system configuration and user interface. The computer software architecture may exhibit independence of the two partitions so that system configuration and user interface actions cannot delay or suspend the real-time sorting functions. This may be accomplished by the primary computer processing all data for all channels simultaneously, or alternatively, by adding dedicated processors for each channel which calculate rapidly in real time and feed processed data to the central computer for integration with other data and information associated with the operation.

According to an aspect of the present technology, a system is provided comprising compressed air ejectors to remove selected particles from the material stream as the stream falls off the end of the belt (or sliders). The spatial pitch of the ejectors is determined by the required resolution of particles to be ejected. Alternatively, as practiced in the art, flip-flop type paddles can be used to eject the particles.

According to an aspect of the technology, a system is provided where an x-ray transmission detector array is utilized to measure x-ray attenuation on passing through a chip and this measurement may be used to estimate chip thickness for use in real-time calibration of fluorescence peak ratios which will vary depending upon chip thickness. Also, the x-ray transmission detector array can be utilized to detect small dense inclusions. This data of thickness when combined with shape from the line scan camera can also determine volume of each piece or chip and thus using appropriate density data can determine the quantity of material sorted into various steams in terms of either volumetric or weight of samples produced for each type in the separation process.

According to an aspect of the application, a system is provided incorporating a dual energy x-ray transmission detector array that can be utilized to find elemental absorption edges that fall between the two energy levels.

According to an aspect of the application, a system is provided including an infeed belt (or one or more gravity-fed channelized sliders), an x-ray source, an x-ray detector array, multiple single-pixel x-ray detectors, detector mounting hardware to position the detectors above or below the material stream, an x-ray collimation system, and an x-ray safe enclosure. Furthermore, the system may include suitable full-speed (full-width across belt or sliders) material presentation at the array of detectors. Fine-pitch ejector nozzles may be used. Paddle flippers and other ejector mechanisms may alternatively be deployed and are known by those skilled in the art.

The x-ray source may include multiple sources arranged to provide uniform radiation across the detectors.

According to an aspect of the technology, methods and apparatus are provided for automatically identifying and sorting small quantities of deleterious contamination from large volumes of titanium, nickel- and cobalt-based "superalloy" scrap without labor intervention.

According to an aspect of the technology, methods and apparatus are provided for removal all superalloys from a mixed stream of titanium scrap aerospace metals. Re-introduction of the high-quality titanium material into processing plants as feedstock for melting furnaces may be performed.

According to one aspect, x-ray driven optoelectronic sensors are used, such as those first developed for and utilized on the Mars Pathfinder space mission. However, such technology may be modified and adapted to the scrap metal business, according to one aspect. According to one aspect, a paradigm shift in the way scrap metal is handled and processed in the U.S. today is introduced, replacing operator touch, feel and visual analysis with high-speed, automated machine analysis.

The transmissive x-ray attenuation characteristics of materials are utilized to achieve identification, and subsequent sortation, of those materials. While the cumulative attenuation from a single x-ray energy region facilitates differentiation between thin and thick pieces of a specific material or between various materials of a similar thickness, the relative attenuation from two x-ray energy regions facilitates differentiation between pieces with a variety of thicknesses and compositions. This "dual-energy" transmission technique for material identification may be used for high-speed sortation to adequately discriminate between metals with significantly different atomic numbers (Z), such as between aluminum (Z=13) and copper (Z=29). For the automotive industry the shredding of automobiles produces an assortment of metals. After ferromagnetic separation the residual "non-ferrous" concentrate (NFC) may be broadly categorized as aluminum, stainless steel, copper or zinc alloys, depending on its dominant constituent. Such dual energy transmission technique may be used to separate mixed aluminum ("Twitch") from mixed "heavy" non-ferrous metals ("Zebra"). However, according to one aspect, identification of metals and alloys does not require a large difference in atomic number. For example, transmissive attenuation from multiple energy regions or x-ray fluorescence at multiple energy regions may be used, avoiding the need to have a very significant difference in atomic number.

One industry which would substantially benefit from high-speed sortation of alloys with similar effective atomic numbers $(Z_{eff})^1$ is aerospace. In the aerospace industry the majority of metals may be categorized as either titanium alloys or "superalloys." While precise segregation within the group of superalloys could prove valuable, significant value may also be obtained by removing all superalloys from a mixed stream of titanium scrap aerospace metals and re-introducing the high-quality titanium material into processing plants as feedstock for melting furnaces. An additional benefit could be realized by further differentiating between titanium alloys and ensuring that elements, "poisonous" to certain grades of titanium alloys, are not inappropriately re-introduced as viable feedstock.

[1] $Z_{eff}$ represents the effective or "average" atomic number of an alloy resulting from the cumulative attenuation by its constituent elements.

According to an aspect of the technology, methods and apparatus are described for automatically identifying and sorting small quantities of highly deleterious contamination from larger volumes of titanium, nickel- and cobalt-based "superalloy" scrap without labor intervention.

According to an aspect, "poisonous" contamination from scrap alloy machining chips is removed using new technology described herein called the CHIPSORT™ technology. The machining chips may be recycled, for example for re-use in the original alloy from which they came; specifically, high-value superalloys which can typically be worth say $5.00 per pound or more.

According to an aspect of the present technology, a method of sorting materials of interest is provided. The method may comprise irradiating pieces of material with incident x-rays and detecting transmitted and fluoresced x-rays. In an embodiment, both the fluoresced and transmitted x-rays are used together (either simultaneously or through iterative convergence) to determine the composition and thickness of the material. In an embodiment, a dual energy (or multi-energy) detector may be used to facilitate such determination of composition and thickness, though in some embodiments a single energy detector may be used.

As have been explained above, various embodiments utilize x-ray transmission and/or XRF data. For both transmission and fluorescence, the "detection mechanism" can be either direct-energy detection or indirect-energy detection. For direct-energy detection, the absorbed x-ray is converted to electrons and the resultant charge is measured. For indirect-energy detection, the x-ray is absorbed by some intermediary substance which then re-emits a portion of the x-ray energy as lower-energy photons (e.g., "visible" photons). It is the re-emitted photons which are directly detected. Furthermore, both direct- and indirect-energy detectors can be categorized according to whether their response is primarily for low- or high-energy x-rays.

For example, suppose it is desired to detect 20 keV (low-energy) and 100 keV (high-energy) x-rays. To detect the low-energy x-rays, direct-energy detectors based in silicon (e.g., Si-PIN, SiLi, SDD) may provide good results in some embodiments (to within a few tens of eV). While the direct-energy detectors based on cadmium would also detect the low-energy x-ray, the noise may result in a larger measurement error (to with a few keV). Since silicon has a low $Z_¬$ value, the probability of absorbing the high-energy x-ray is very low. In contrast, the high $Z_¬$ value of cadmium offers a high probability of absorbing the high-energy x-ray. Typically, the higher noise of cadmium-based detectors is not a significant issue at the higher energy.

For indirect-energy detection the intermediary substance is typically a layer of "phosphor" material. Some readily available phosphors are based on gadolinium (Z=64), which re-emits near 500 nm. Since silicon detectors efficiently absorb "visible" photons, bonding the gadolinium material to a silicon detector conveniently results in an "x-ray detector". While this form of detector could be used to discriminate between the 20 and 100 keV x-rays, the count rate may preferably be very slow (on the order of 1,000 x-ray events per second). Instead of measuring the energy of each x-ray, this type of detector may be better for measuring the integrated energy of many photons, over a potentially wide energy range.

In some embodiments, detectors may be stacked, for example to facilitate dual-energy detection. Stacking indirect-energy detectors may result in the first detector absorbing almost all low-energy x-rays, such that the signal from the second detector is composed from more high-than low-energy x-rays. By stacking these detectors, the first detector has a "low-energy absorption" profile while the second detector has a "high-energy absorption" profile. In a very coarse manner, one can shape the absorption profiles of the two detectors. For example, a very thin phosphor layer on the first detector would allow more high-energy x-rays to pass to a thicker layer on the second detector. Similarly, a low-Z phosphor on the first detector would allow high-energy x-rays to pass. Physically arranging the detectors in a stacked configuration, as an example, thus facilitates acquisition of dual-energy data.

The aspects described above, as well as additional aspects, are described further below. These aspects may be used individually, all together, or in any combination of two or more, as the technology is not limited in this respect.

The following description provides additional details. For purposes of illustration, the following description focuses on sortation of metals, though it should be appreciated that aspects of the present technology apply to other materials. Furthermore, for purposes of illustration, the following description focuses on using certain component parts (e.g., an Amptek detector, a NEXIS detector module, a Monoblock x-ray source, etc.). It should be appreciated that the specific component parts described below are provided for purposes of illustration, and are not limiting of the various aspects described. Other types of x-ray sources, x-ray detectors, and other components may additionally or alternatively be used.

Moreover, the following documents are incorporated herein by reference in their entireties: U.S. Pat. Nos. 8,144,831; 7,848,484; 7,564,943; 7,099,433; 7,763,820; 6,888,917; PCT Publication WO2011/0159269; and U.S. Provisional Application No. 60/549,089 filed Mar. 1, 2004 by David Spencer et al. and entitled "High speed non-ferrous metal sorting using XRF".

As used herein, a spectrum is one or more peaks of raw or calculated or normalized XRF (or other x-ray or emissions) data which is greater than both background and extraneous emission data. A spectrum may be used, as described herein, to determine the presence of one or more elements within the periodic table or compounds or mixtures containing one or more elements from the periodic table of elements.

Embodiment of Equipment

Figure 24:
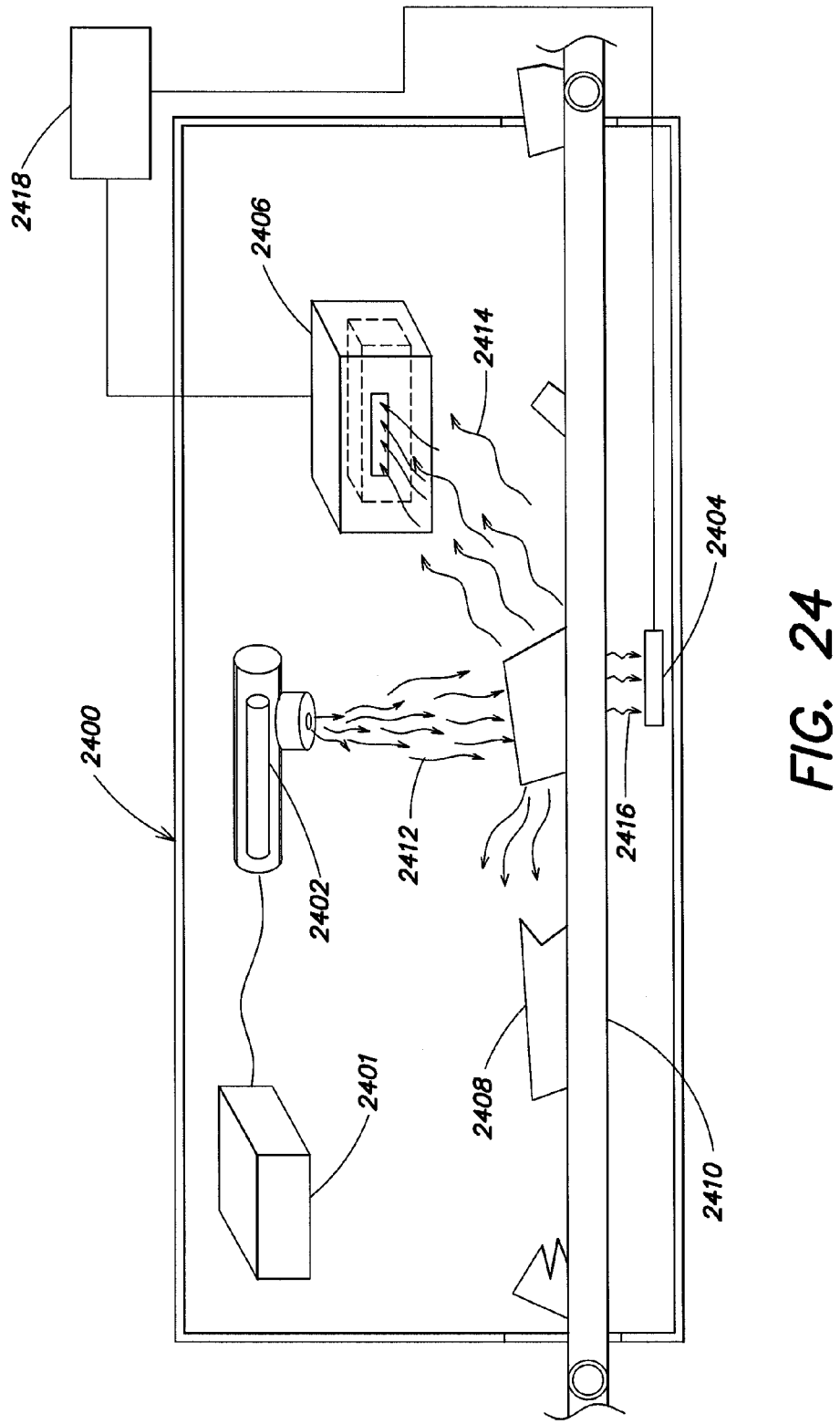
FIG. 24 illustrates a schematic view of a sorting system, according to a non-limiting embodiment.

FIG. 24 illustrates a non-limiting embodiment of a sorting system according to an aspect of the present technology. The sorting system 2400 includes an x-ray source 2402 coupled to a controller 2401, a transmission x-ray detector 2404, and an x-ray fluorescence detector 2406. Pieces of material 2408 are conveyed by a conveyor 2410 into an irradiation zone (inspection zone) in which they are irradiated with incident x-rays 2412. Fluoresced x-rays 2414 are detected by the XRF detector 2406, and transmitted x-rays 2416 are detected by the transmission x-ray detector 2404.

The XRF detector 2406 and transmission x-ray detector 2404 may be one or more of any suitable types of detectors, such as any of those described. One or both of the XRF and transmission types of detectors may be an array or arrays of detectors.

The XRF detector 2406 and transmission x-ray detector 2404 may produce output signals based on the detected x-rays, which may be provided to a processor 2418, which may process the data (x-ray transmission data and XRF data) in any suitable manner, such an in any manner described herein. The pieces of material 2408 may be sorted in response to the processing.

The conveyor 2410 may be any suitable type of conveyor and may operate at any suitable speed. In one embodiment, as shown, the conveyor may be a single conveyor. In an alternative embodiment (FIG. 25A), the conveyor may include two or more distinct segments. For example, conveyor 2500 includes separate segments 2502a and 2502b having a gap between them. The piece of material 2408 may be conveyed to jump the gap. The piece may be irradiated while jumping the gap, and the detectors may be positioned in any suitable manner (e.g., below the gap) to facilitate detection. An atmosphere or vacuum may be utilized to enhance signal strength and windows may be used as described herein for materials handling or for containment of atmosphere or vacuum.

The segments 2502a and 2502b may be at substantially the same height as each other, or at different height.

In the embodiment of FIG. 25B, which represents a top-down view of a conveyor, the conveyor may include a window 2512 and/or a mesh segment 2514, either or both which may be used to facilitate irradiation and/or detection of x-rays of pieces of material. The window may include a cover in some embodiments, which may be made of soft or hard material, such as polymers, beryllium, ceramics, diamond (e.g., or other hard, abrasion resistant material) or other highly transmissive thin films. Any cover over a window or opening of a conveyor may be highly transmissive to x-rays.

FIG. 25C illustrates a further example, in which the conveying system 2520 includes two conveyor belts 2522a and 2522b in parallel, such that pieces of material 2408 can straddle the gap between them.

Any combination of feature of the conveyors shown in FIGS. 24, 25A, 25B, and 25C may be used.

According to a first non-limiting embodiment, the acquisition of x-ray information may be performed using a detector, such as a XR-100T-CZT model detector from Amptek, a CZT-based NEXIS detector module from Nova R&D, and a 480 W Monoblock x-ray system from Spellman. The Amptek detector is a single "pixel" device which records an x-ray spectrum as a histogram of x-ray events occurring within 1024 energy bins. The acceptable x-ray count-rate for this device is around $10^4$ (10 k) counts per second. The NEXIS (N-Energy X-ray Image Scanning) module is a new sensing technology. The advantages of this module, as compared to an Amptek detector, are twofold. First, this detection module provides 256 detectors which are physically arranged as 2 rows of 128 "pixels" with a 1 mm detector pitch. Thus, each column can produce a 128-by-N image, where N is an arbitrary number of frames. Second, the supporting electronics for each of the 256 detectors can resolve $10^6$ (1,000 k) counts per second, albeit for only five energy bins. With the NEXIS system one can obtain a multi-energy x-ray transmission image with high spatial resolution and at a high flux.

It should be appreciated that in some embodiments a sorting system does not use two rows of x-ray fluorescence detectors. Rather, a single row of detectors may be used. When two or more rows are used, they may be adjacent and parallel to each other in some embodiments, or stacked, not adjacent or not parallel in others such as staggered.

An enclosure may be included to house the Monoblock x-ray system and the detectors. Alternatively monochromatic sources may be used from radioactive isotopes or produced by DCCs. Within the enclosure a conveying belt may transition samples through the detector's field-of-view to record the x-ray transmission characteristics of those samples. The acquired spectra may then be processed by MatLab and/or other suitable software to produce an analysis and identification of the material.

The majority of aerospace scrap material targeted for reclamation is in the form of machining chips. These chips are nominally flat, but with some curvature, with a width and length on the order of 6 mm and a thickness of 0.4 mm. According to one aspect, we separate chips of titanium alloys from those of superalloys by comparing their x-ray scattering properties at various energy regions. According to one non-limiting embodiment, by examining the spectrum from chips (e.g., the x-ray fluorescence spectrum) acquired at a 45° angle from direct transmission, the x-ray fluorescent peaks from the various constituents may be evident although superimposed on a background of scattered x-rays. The peaks in this "off-angle" XRF spectrum permit accurate identification of composition for the material allowing for separation into its elemental or alloy constituents. Thus, such techniques may be used, for example, to separate groups having a small difference in $Z_{eff}$ and thinness (e.g., $Z_{eff} \approx 22$ for titanium alloys and $Z_{eff} \approx 26$ for the superalloys (composed primarily of chromium, iron and nickel)). Such sorting may be performed at speeds reasonable for commercial high speed sortation.

A significant, but lower volume, segment of aerospace scrap material is in the form of "cobbles". These pieces are several times larger than chips, with a thickness range of between 1 mm and 15 mm Off-angle spectrum analysis, as described above, renders possible sortation of these types of materials as well from the superimposed XRF peaks.

According to another non-limiting embodiment, separation of titanium alloys is performed; particularly, the separation of tin-bearing titanium alloys from those containing no tin. Separation may be based on an examination of the transmission spectrum around the x-ray absorption edge of tin (29.2 keV). If a discontinuity exists, tin is present in the alloy. Successful detection of alloys containing only 2% tin may be made with the Amptek detector using XRF.

According to another non-limiting embodiment, separation focused on NFC from automotive shredders. Since this material is at least as thick as cobbles, transmission-based separation of Twitch from Zebra was successful. For successful sortation of the Zebra components, we returned to the off-angle spectra and found information at the XRF peaks of iron, copper and zinc allow identification of the various metals and alloys in the Zebra fraction.

Sortation based solely on x-ray attenuation as measured by an energy-dispersive x-ray detector, such as the Amptek and NEXIS, is possible. However, a commercially viable, high-speed sorting system for distinguishing between alloys with only slight differences in $Z_{eff}$ would require a significant increase to the count-rate limitation of current technologies. In contrast, a hybrid sorting system, constructed from current technologies (which may include one or more of the following detectors: Cadmium Telluride (CdT), Cadmium Zinc Telluride (CZT), SiLi and Silicon Drift (SDD) detectors), that also employs transmission data for "rough" sortation between materials with a large difference in $Z_{eff}$ or detecting inclusions and off-axis XRF data for "fine" sortation between materials with small changes in metal concentrations may be used. In addition, the NEXIS system is particularly adept at producing an "x-ray image" of the sample showing items such as "holes" or "inclusions" or "surface coatings" having different x-ray absorption characteristics thus allowing sortation to also be conducted based on analysis of these x-ray images as well as based on transmission and XRF data collected. Alternatively dual energy or differential energy transmission detectors can also be used in place of the NEXIS system with acceptable and sometimes even better results. For example, dual-energy transmission detectors of the types previously described (e.g., stacked phosphor-on-silicon) or any other types may be used.

The techniques described herein may be used to exploit differences between the most predominant alloys found in the aerospace industry and in the recycling of automotive-shredder scrap for effective sortation. These techniques are also applicable to sortation of mineral ores, glass, and many other materials as well.

According to a non-limiting embodiment, a single-channel acquisition system, comprising or consisting of a Monoblock x-ray source and CZT detector from Amptek, allows for acquisition of both transmission and XRF spectra. XRF-based sortation may be used successfully. A multi-channel acquisition system, comprising or consisting of a Monoblock x-ray source and the CZT NEXIS detector array from Nova R&D, allows acquisition of transmission spectra. A comparison of the performance of the two detectors indicates that the NEXIS module can accommodate a much higher counting rate but exhibits more noise and is less sensitive to energies below 30 keV than the larger and more expensive Amptek CZT detector. Comprised of multiple detectors arranged in a "close" spatial proximity, the NEXIS module does provide a high-resolution "image" of x-ray data. Note that a closely spaced "pixel" configuration of the AMPTEK detectors can collect the same type of imaging data as the NEXIS systems and further that AMPTEK detectors such as the SiLi and SDD detectors produced by AMPTEK and others have advantages over the higher energy level CdT and CZT detector at lower Z ranges. For energy ranges below 30 keV these other types of detectors may be used alone or in combination with CdT and CZT detectors to gain added XRF information with less background noise and will result in capture of more data as a result of their greater sensitivity to XRF signals and higher spectrum count rates at lower energy ranges. The disadvantage with these detectors as produced today is that they are not very sensitive making measurements above the 30 keV range as compared to the CdT and CZT detectors produced today. Thus, the CdT and CZT detectors may optimally be used in combination with the SDD and SiLi detectors, for example to enable an extended energy detection range.

According to an embodiment, sorting titanium chips when various contaminants were present is described. Successful detection of deleterious contaminants such as tin-bearing titanium alloys containing only 2% tin and very small tungsten inclusions or particles within a matrix of clean titanium chips was performed. The capability of effecting identification of tin contaminants has never before been demonstrated and thus this seminal work may be used in a commercial system with tremendous value to the titanium and superalloy industry. Moreover, the potential of detecting small tungsten inclusions at high speeds within a fully automated process has never before been demonstrated using dual energy or DXRT transmission sorters. Not only may tungsten (W) be detected using the technology described herein, but also other "Refractory Metals" such as molybdenum (Mo), Tantalum (Ta) and others. For mining applications these Refractory Metals may be sorted notwithstanding the fact that they are present for example as sulfides or oxides since the sulfur and oxygen are not likely to impact the signal due to absorption in air.

Applicants have found that transmission data is sufficient for segregating NFC into Twitch and Zebra. Copper and zinc in aluminum alloy A380 could be detected by their XRF signature and sorted accordingly as could the various alloys in the Zebra fraction.

There are two aspects of characterizing an alloy from its transmission spectrum: elemental constituents and $Z_{eff}$. The detection of an element's absorption edge indicates its presence within the alloy. This method was employed to distinguish tin-bearing titanium from Ti CP and Ti 6-4. The $Z_{eff}$ of an alloy quantifies its absorbance relative to elements and facilitates the separation of high-Z alloys from low-Z alloys. This method was employed to separate Twitch from Zebra. However, as the required resolution for distinguishing between the $Z_{eff}$ of material groups increases the counting statistics must also increase. Since this increase in statistics is typically purchased with a decrease in productivity, finer separation of $Z_{eff}$ yields lower volumes. The new sorting technologies using x-ray transmission that are described herein can sort materials that are far apart on the periodic table or alternatively which are closer together but have an absorption edge between them. That is to say, a. The materials may have an absorption edge between the two energy ranges being employed such that the differences between the two materials is accentuated when they are close on the periodic table, or b. The materials may need to be far enough apart on the periodic table that the absorption characteristics of the incoming x-rays create sufficient signal differences, given the inherent system noise of the detectors and the thickness of the pieces, to accurately distinguish one particle from another. However, the use of newer detectors which may be under development may reduce these limitations in the future.

Using the state of the art for the latest detectors available in the field (such as the Nova R&D NEXIS system and the Amptek CZT detectors), using measurement of multi-energy transmissive attenuation may facilitate:

a. Removal of tungsten inclusions or tungsten particles from a matrix of titanium chips at high speeds and at commercial volumes.

b. Sorting tin-bearing titanium alloy chips from non-tin-bearing titanium alloys or chips. The workhorse titanium alloys are commercially pure titanium (CP) and 6-4 titanium. When these are contaminated with tin-bearing titanium alloys they lose much of their value. We can identify and thus effectively sort out chips containing only 2% tin from chips containing no tin through absorption edge detection.

c. Sorting mixed non-ferrous metal concentrates from an automobile shredder into a light fraction and a heavy fraction. In the case of sorting Zorba feedstock (mixed non-ferrous metal alloys from an automobile shredder) into (1) "lights" or Twitch (mixed aluminum) and (2) "mixed heavies" or Zebra (stainless steel, nickel, copper and/or zinc), this new technology is useful. Multi-energy technology may be better and the signal more informative than dual-energy technology.

d. Dual energy and Multi (more than two) energies used for transmission analysis may be useful in determining particle thickness which is also useful in normalizing data from thin chips for accurate XRF identification of unknown alloys.

Figure 4:
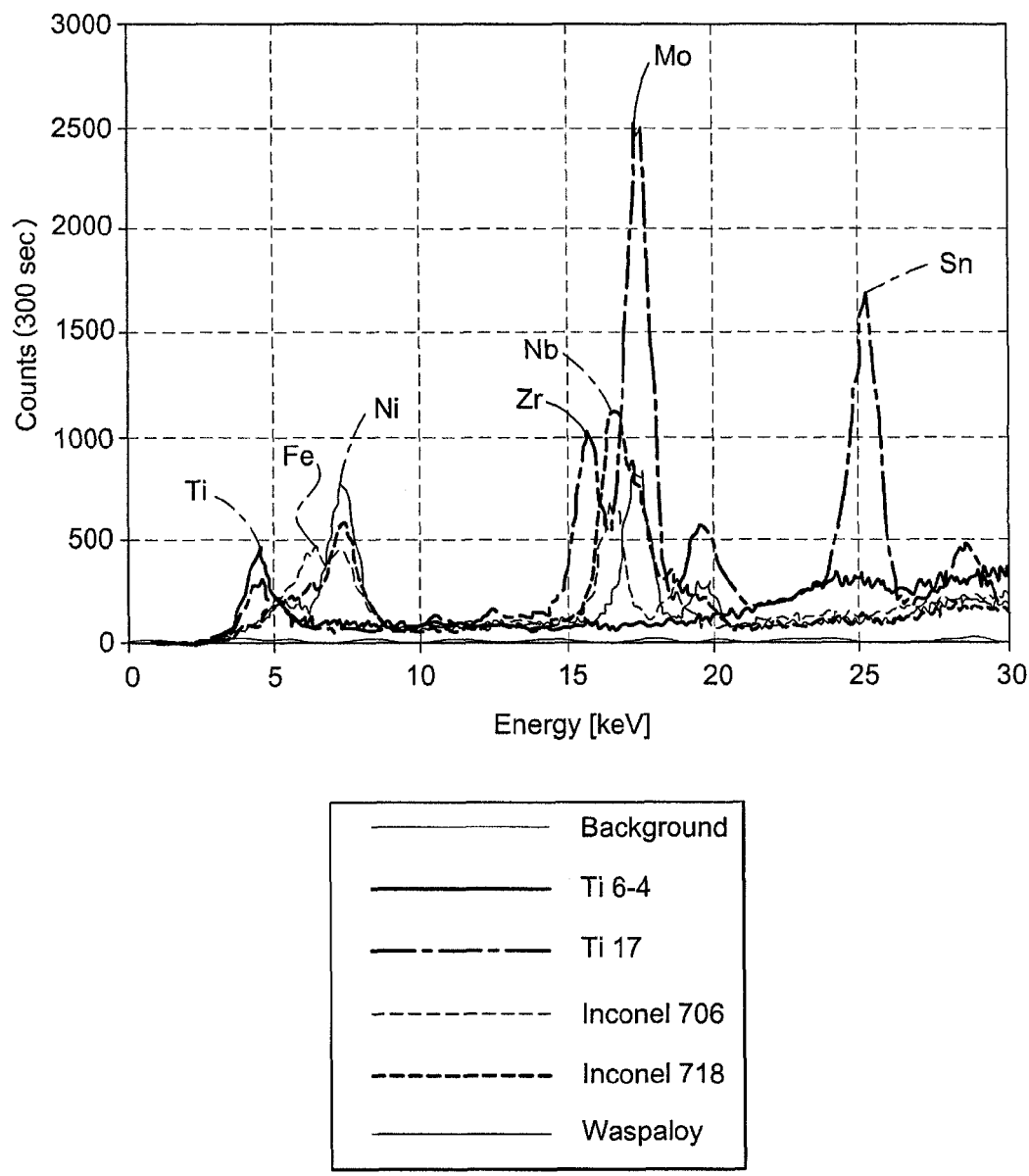
FIG. 4 provides the XRF spectra for several chips whose thickness is approximately 0.25 mm

According to one aspect, we acquire x-ray fluorescence from small particles using new systems and new configurations that can differentiate materials that are close on the periodic table even when the pieces are very small and have thin cross sections, such as aerospace alloy turnings. This provides an innovative approach to the massive commercial opportunity for sorting mixed chips of superalloys and titanium alloys at commercial feed-rates. FIG. 4 provides the XRF spectra for several (machining) chips whose thickness is approximately 0.25 mm. From the data shown in FIG. 4 it is evident that the location of the fluorescent peaks along the Energy [keV] axis and relative height of the fluorescent peaks facilitate robust identification of the various alloys.

Sortation of aerospace turnings presents a very large commercial opportunity. According to one embodiment, a system includes both identification and sortation capabilities suitable for modest commercial scale operations. According to one embodiment, we also simultaneously, with the same hardware, enhance the information output to include imaging information.

According to one non-limiting embodiment, we describe a unit that demonstrates the fundamental requirements for producing a commercially viable, high-speed and high-volume system for the sortation of titanium and superalloy machining chips. An important, and in some cases primary, function of this system is to separate a stream of chips according to a desired grouping of alloys, for example separation of a titanium group of alloys from a superalloy (nickel-cobalt based) group of alloys. A secondary function is to purify the stream through removal of any commingled contaminant chips. In such cases, with dilute contamination by "poisonous" elements it is not a significant disadvantage to remove many good chips with the few bad chips.

According to one embodiment, a mechanism which appropriately distributes and conveys a stream of metal chips for presentation to a multi-channel XRF detection array (i.e., XRF line scan camera) is provided.

According to another embodiment, an optimal sensing configuration for measuring energy dispersive XRF spectra from metal chips in real-time as they transition a multi-channel (defined in the art as simultaneously having parallel material flow down many parallel channels, each containing its own detection sensor) detection area at rates required for commercial sortation is provided.

According to another embodiment, a sorting unit which consists of a presentation mechanism, a multi-channel array of energy dispersive XRF detectors (XRF line scan camera) and real-time data acquisition hardware and utilizes real-time computer analyses of the XRF data to effect a precise pneumatic ejection of selected chips from the stream is provided.

According to one embodiment, a commercially viable, high-speed system for sortation of machining chips (e.g., typical aerospace machining chips), based solely on x-ray attenuation, which not feasible with conventional technologies, is described. Extremely high count-rates may be beneficial (and in some cases, necessary) for accurately measuring the slight attenuation offered by thin material. An x-ray fluorescence spectrum is sufficient to identify the particular alloy of a chip, even with a significantly reduced count-rate.

The detection of x-ray fluorescence provides extremely accurate evidence that a particular element is present. When a high-energy x-ray coerces the expulsion of an electron from its shell within an atom, the atom recruits another electron from an outer shell to fill the vacancy and thereby increase its stability. The transition of an outer electron to an inner shell simultaneously produces an x-ray whose energy is the difference between the binding energies of the two associated shells. Since each element possesses a unique set of binding energies, the energy of a fluoresced x-ray positively identifies the element from which the x-ray originated. Extracting these "fingerprints" (also termed "spectral image" or "spectral pattern" comprising one or more energy peaks) from spectra is a feature, and in some cases a key feature, of our sortation methodology.

Figure 5:
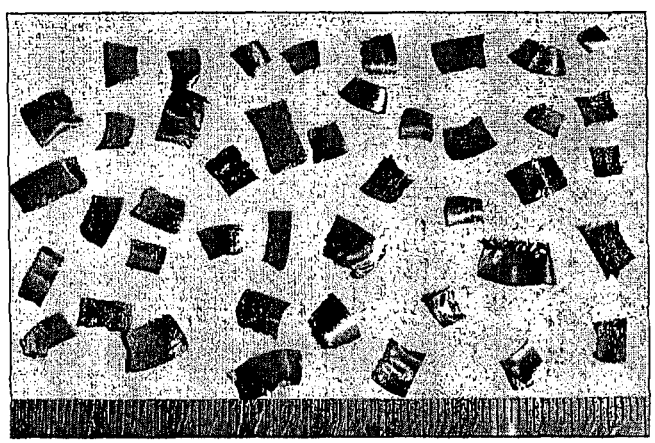
FIG. 5 is an image containing a sample of titanium chips.

The thinness of a chip may impede transmission-based identification. How does the same thinness affect XRF-based identification? One can estimate this influence through considering the attenuation of x-rays by a layer of filtering material. The thickness of a titanium filter required to reduce the 4.51 keV fluoresced x-rays of titanium to ten percent is only 0.05 mm. Therefore the detectable XRF radiation emanating from a titanium chip comes from a surface layer of material only 0.05 mm thick. Similarly, a tin filter of 0.28 mm is required to diminish the 25.27 keV x-rays of tin to ten percent. Yet, the same 25.27 keV fluoresced x-rays from tin require a titanium filter of 0.64 mm to achieve the same reduction of flux. One can infer then, that with titanium chips the detected fluorescence flux at 4.51 keV is practically the same for any chip thicker than 0.05 mm. However, with tin-bearing titanium chips the flux at the 25.27 keV tin fluorescence peak increases until thickness is greater than 0.64 mm. In effect the ratio of the height of the tin fluorescence peak to that of the titanium fluorescence peak increases with chip thickness up to about 0.64 mm thickness. Using peak ratios to determine sample chemistry then becomes problematic for varying chip thicknesses below 0.64 mm thickness, which may make it difficult to successfully distinguish between chips having the same elements but at different concentrations, for instance distinguishing titanium chips with 2% tin from those having 4% tin composition. According to one embodiment, we correlate XRF measurements with chip thickness, obtained from measurements of x-ray attenuation upon passing through a chip, to dynamically adjust peak ratios according to chip thickness. An image containing a sample of titanium chips, and metric ruler, are shown in FIG. 5. Ideally, these "rectangular" pieces would range from 5 to 10 mm on a side and from 0.15 to 0.5 mm in thickness. Due to their small size, the spatial resolution of an applicable XRF array would preferably be somewhere in the range of 1 to 5 mm.

The NEXIS detection module offers a spatial resolution of 1 mm, but suffers from noise and acquisition capability. According to one embodiment, the list of elements we identify ranges from titanium (Z=22) to tin (Z=50) with corresponding fluorescent values between 4.51 and 25.27 keV. Unfortunately, since the NEXIS module is designed primarily for energies above 40 keV, any detected x-ray signals within the desired fluorescence range are inextricable from the noise. Furthermore, the NEXIS module only provides five energy regions for acquiring spectra. Inspection of FIG. 4 suggests that more (and in some cases, many more) regions may be required. Still, the NEXIS system provides excellent visual imaging of the x-ray information that may be valuable in providing additional sortation information.

According to one embodiment, we provide an "x-ray line-scan camera" composed from a linear array of x-ray detectors. Each detector, or "pixel", provides an x-ray spectrum by acquiring the energy distribution of fluoresced photons that impinge on that detector. Concatenation of these spectra results in a "scan-line" of spectra. A high-speed digital communication interface may then transfer each scan-line to the sorting computer at approximately 500 scans per second. The sorting computer may assemble successive scans into a two dimensional image, and then operate on that image to make the material sortation decisions such as detection of inclusions in a piece of material (for example, a tungsten inclusion in a piece of titanium from a broken drill bit).

Each pixel in the scan contains the energy distribution values needed to extract significant x-ray fluorescence peaks that identify the elemental constituents of the material passing the detector array. A sorting algorithm based on a peak's location and relative height within a small area of the x-ray image will trigger an ejection system that removes the corresponding material from the material stream.

The high-speed x-ray line-scan camera described here is entirely novel. While x-ray area-scan cameras are available, they are intended for applications such as astronomical or medical observations where the rate of image capture is relatively slow. Our technology provides an image acquisition rate at least on the order of 480 Hz where each image comprises an energy distribution spectrum from each pixel. A line-scan camera system may comprise 120 pixels (for a 30 inch belt at 0.25 inch detector spacing) where each pixel generates a 512 bin energy distribution histogram of 16-bit energy values. In this case, the data rate from the camera is 120×512×16 bits (or 960 Kbits) every 2.08 millisecond (msec) for an aggregate of 450 Mbits per second. Obviously, if it is determined that the detector spatial pitch must be even less (as may be the case when processing chips on the smaller end of the target range), then the data rate goes up accordingly. These are very high data rates based on current technologies. Furthermore, after the scan-line of data is transferred from the camera to the sorting computer, a sortation decision is computed every few frames, perhaps every 5 frames for a decision every 10 msec, and the results issued in the form of control signals sent to ejector control hardware. These very high image acquisition, data transfer, decision computation, and ejection control rates are useful to successful sorting. The high-speed x-ray line-scan camera is a valuable new instrument with applications in other XRF-related analysis and processing fields.

The following tables (Tables 1-3) show a selection of data rates computed across a varying belt width and number of energy histogram bins. The tables also show the resultant material flow-rate.

Figure 2:
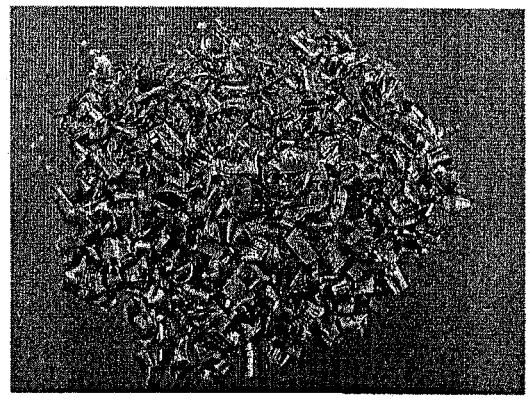
FIG. 2 illustrates superalloy machining chips resulting from shredding and cleaning of machine turnings of the type illustrated in FIG. 1.
Figure 3:
FIG. 3 illustrates material pieces to which aspects of the present application may be applied.

Constants: belt speed is 10 ft/sec
pixels are 0.25 in x 0.25 in
chip density is 0.10 g/in$^2$ (as seen in FIG. 2)

For energy histograms of 1024 bins with 16 bit values from each bin:

TABLE 1

| Belt width (in) | Num. detectors | Flow (lb/hr) | Data rate (Mb/sec) |
|---|---|---|---|
| 6 | 24 | 570 | 180 |
| 12 | 48 | 1140 | 360 |
| 30 | 120 | 2850 | 900 |

For energy histograms of 512 bins with 16 bit values from each bin:

TABLE 2

| Belt width (in) | Num. detectors | Flow (lb/hr) | Data rate (Mb/sec) |
|---|---|---|---|
| 6 | 24 | 570 | 90 |
| 12 | 48 | 1140 | 180 |
| 30 | 120 | 2850 | 450 |

For energy histograms of 128 bins with 16 bit values from each bin:

TABLE 3

| Belt width (in) | Num. detectors | Flow (lb/hr) | Data rate (Mb/sec) |
|---|---|---|---|
| 6 | 24 | 570 | 23 |
| 12 | 48 | 1140 | 45 |
| 30 | 120 | 2850 | 113 |

The number of requisite energy histogram bins may be determined in any suitable manner. In general though, a higher precision to distinguish between elements with neighboring XRF peaks requires a higher number of histogram bins.

Single-pixel detectors with integrated energy distribution data collection hardware are available from multiple manufacturers, including Amptek and Nova R&D, but a multi-pixel detector array with the necessary 1 mm to 5 mm pitch was not previously available. According to one embodiment, we design and implement the sensor array and interface hardware to transfer the data from an array of detectors to the sorting computer at high speed using one of the available single-pixel detectors.

Furthermore, various embodiments may include the following:
1. Separating titanium alloys containing more than a few percent of tin.
2. Optimizing the trade-offs between sample presentation time, x-ray source power settings, detector energy resolution, detector count-rate, and detector dead-time (detector response speed). Each of the parameters affects the others. To maintain the targeted material throughput, the presentation time will preferably (and in some cases, necessarily) be short (on the order of 1 msec); the other parameters may be (and in some cases, must be) adjusted (and the sortation algorithm be so constrained) to accommodate the short-time or "immature" spectra captured under these conditions.
3. Providing the best collimation scheme to reduce the "bleed-over" of XRF photons from one detector to the next. At the high spatial resolution required for small chips, the fluorescence photons at one detector element can easily influence the detector next to it. Some embodiments provide an effective collimation system to isolate each detector element as much as possible.

Figure 6A:
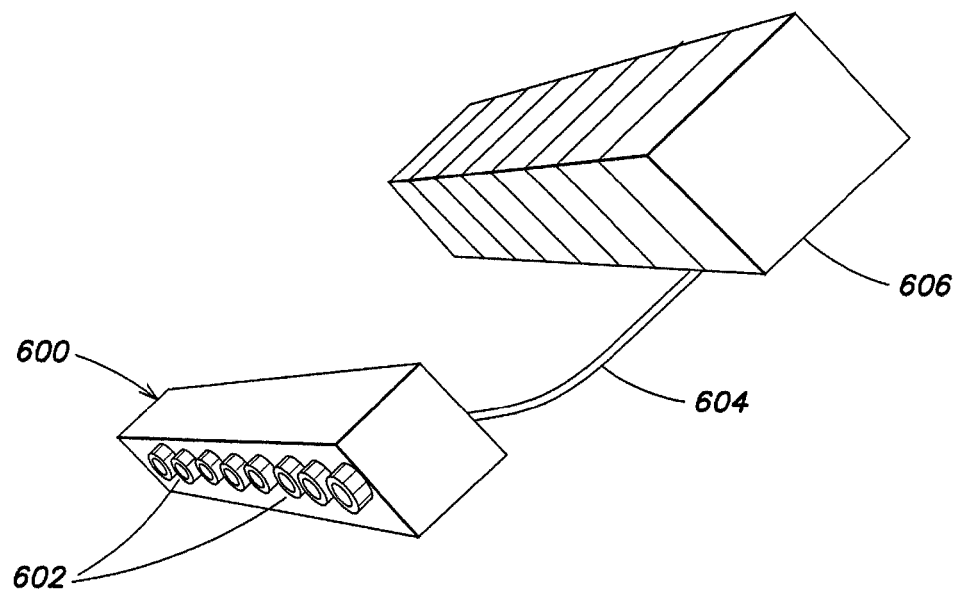
FIG. 6(a) shows a conceptual sketch of an XRF detector line array with the row of detection elements each collimated by a tubular collimator, according to one non-limiting embodiment.

FIG. 6(a) shows a conceptual sketch of an XRF detector line array 600 with the row of detection elements each collimated by a tubular collimator 602, according to one non-limiting embodiment. Chips are distributed on the belt such that optimally only one chip is sensed by the pixel(s) or detector(s) for one channel or pathway from among the multiple channels placed across the width of the entire belt or conveyance device (which could also be one chute from among many parallel chutes). The purpose of a collimator 602 is to expose a given detector array sensing element to only fluoresced x-rays emitted from its corresponding "pixel" location on the belt surface by blocking out any fluoresced x-rays emitted from other locations on the belt surface. The detector array 600 contains the arrayed pixelized detector elements and their preamplifier circuits. The detector array 600 is connected by a wiring harness 604 to the detector array signal electronics 606 where electronic signals from the detectors are conditioned and parsed into energy bins.

Figure 6B:
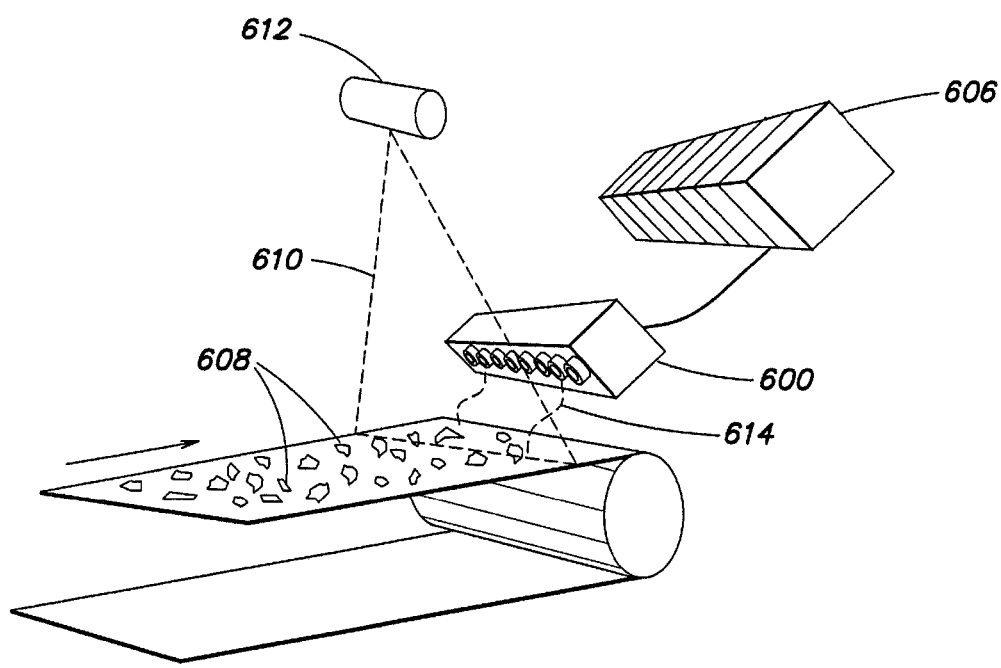
FIG. 6(b) shows the array positioned over a conveyor belt carrying a random dispersed distribution of alloy turning chips through an x-ray sheet emanating from a source directed onto the belt along the pixel line being viewed by the detector elements of the detector array.

FIG. 6(b) shows the array 600 positioned over a conveyor belt carrying a random dispersed distribution of alloy turning chips 608 through a collimated x-ray sheet 610 emanating from a source directed onto the belt along the pixel line being viewed by the detector elements of the detector array 600. (Multiple detectors for each channel may also be deployed to expand the energy detection counts or increase sensitivity across a wide range of energy levels.) The detector array 600 is positioned "off-axis" from the x-ray sheet 610 so to not interact with source x-rays. X-ray photons from the (collimated) x-ray source 612 irradiate alloy turning chips 608 as they pass through the x-ray sheet 610 at the pixel line. The irradiated alloy chips absorb x-rays from the x-ray sheet 610 and re-emit fluoresced x-rays 614 particular to the elemental constituents of each of the chips 608. Fluoresced x-ray photons travel to the detector array 600 and pass through the collimator open path to the detector element "viewing" the pixel location along the belt where the chip is located. The detector element interacts with the fluoresced x-ray photons and the detector array signal electronics 606 measure the energy of each photon thereby building up a spectrum of the fluoresced x-rays 614 emanating from the alloy chip at its pixel location. The spectrum is passed to a high-speed computerized system (not shown) which analyzes spectra as they are generated and issues directions to a sorting system according to a chip's composition in order to sort the chips 608 by composition. According to one embodiment, a 24 pixel XRF line scan camera having approximately 6" sensing width is provided for a sortation system. Other arrangements for positioning the detectors, x-rays source, and particles within an apparatus will be apparent to those skilled in the art.

Figure 7:
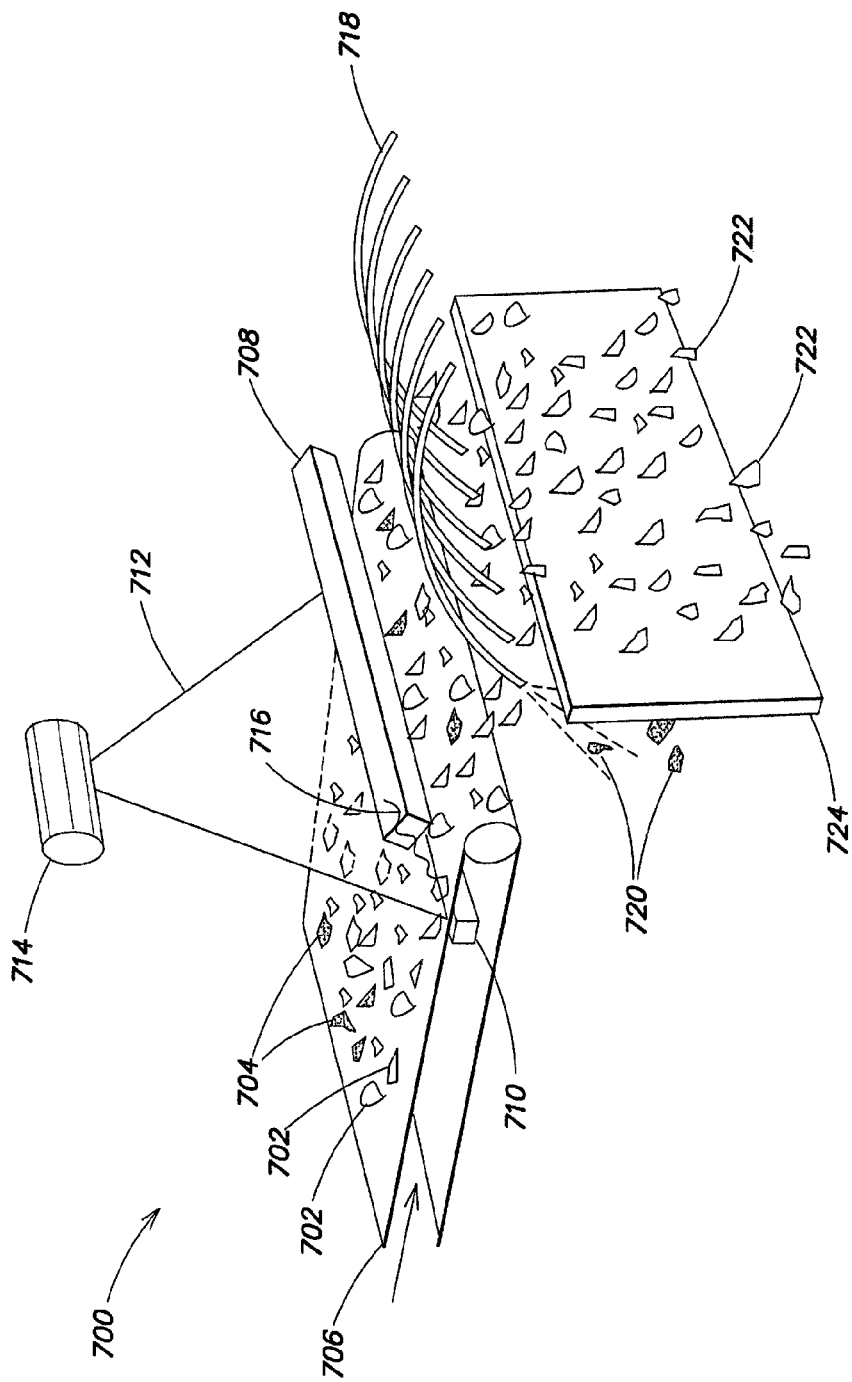
FIG. 7 illustrates a sketch of a configuration of a sorter for sorting alloy chips according to one non-limiting embodiment.

A sketch of a configuration of a sorter for sorting alloy chips according to one non-limiting embodiment can be seen in FIG. 7. In particular, FIG. 7 is a conceptual sketch of a sorting system configuration 700 incorporating an off-axis positioning of a 24 pixel XRF line scan camera for identification of alloys in a stream of product alloy turning chips and a transmission x-ray sensing array enabling real-time measurement of chip thickness to calibrate XRF peak ratios and detection of dense inclusions such as tungsten-carbide tool bit pieces. The stream of product alloy turning chips may include product chips 702 and contaminant chips 704.

The material to be sorted passes through the detection area via a flat conveyor belt 706 (or alternatively a channelized gravity-fed slide). XRF photons emitted from a sample are acquired at the "off-axis" x-ray fluorescence detector array 708 contained in a 24 pixel x-ray line-scan camera (note: for clarity the signal electronics are not shown). The scan-line image is transferred to the sorting computer over high-speed communications channel. The sorting computer executes the material classification algorithms and sends control signals to the compressed air ejection system where the identified material is removed from the main stream of material moving off the end of the belt 706. An "on-axis" detector array 710 positioned under the conveyor belt 706 provides the option of integrating x-ray transmission attenuation data and XRF information to effect calibration of XRF signal peak ratios according to chip thickness and to identify (e.g., through x-ray imaging such as is done for airport security systems) contaminant chips 704, for example small dense inclusions such as tungsten carbide tool pieces.

In an embodiment, the system features may include:
1. Preferably, and where unambiguous sorting is required, a material presentation system that may be either a flat belt or 706 a group of channelized gravity-fed sliders. The material particles are preferably presented to the detectors in a non-overlapping single-layer manner.
2. An array of closely-spaced x-ray detectors 708 positioned perpendicular to the material flow off-axis to the x-ray beam sheet 712 so that x-rays emanating from the x-ray source 714 do not interact with the detectors. The array of detectors 708 functions as an x-ray line-scan camera by acquiring an energy distribution histogram for each pixel in the detector array 708 as fluoresced x-rays 716 emanate from irradiated alloy turning chips passing through the source x-ray sheet beam 712. An updated set of histograms, or spectra, are transferred to the sorting computer for each scan-line of the acquisition process. Each detector element in the array 708 is shielded by collimation such that only XRF photons from samples directly "beneath" that detector are accepted. X-ray photons from other regions, especially from neighboring pixel areas, are blocked with collimators. A fine pitch x-ray transmission array 710 may be positioned underneath the feed stream of materials to estimate chip thickness from x-ray attenuation and for detection of small dense inclusions which may be too small to produce sufficient x-ray fluorescence flux to be measurable by the XRF line scan camera.
3. A sorting computer with hard real-time processing capability. The computer includes an isolated partition dedicated to the sorting task, which preferably (and in some cases, must) execute within guaranteed timing and latency constraints, and another partition that does system configuration and user interface. The computer software architecture may exhibit independence of the two partitions so that system configuration and user interface actions cannot delay or suspend the real-time sorting functions. This may be accomplished by the primary computer processing all data for all channels simultaneously, or alternatively, by adding dedicated processors for each channel which calculate rapidly in real time and feed processed data to the central computer for integration with other data and information associated with the operation.

4. A system of compressed air ejectors 718 to remove selected particles 720 from the material stream 722 as the stream 722 falls off the end of the belt 706 (or sliders) past a product splitter 724. The spatial pitch of the ejectors 718 is determined by the required resolution of particles 720 to be ejected. Alternatively, as practiced in the art, flip-flop type paddles can be used to eject the particles 720. Other ejection methods will be apparent to those skilled in the art.

Target Materials to be Identified

Robust separation is feasible between materials with significant tin or tungsten components and titanium alloys without those elements. The material goals may also extend to other elements. Target materials include titanium alloys as well as the most important superalloys. The system may optionally be used to sort high temperature (Refractory Metal) alloys, Rare Earth Elements (also called Strategic Metal Alloys) or other materials of interest, either metal or non-metal such as mineral ores and glass.

Data Features Useful to Separate the Particles and the Method(s) to Extract Those Features from X-ray Fluorescence Spectra.

Data feature definitions may be described to facilitate detection. We can estimate both the envelope of and interaction between operational parameters for effecting a desired sortation.

Material Flow-rate and the Data Rate Useful to Satisfy System Target Goals.

The required belt width and corresponding flow-rate of the material through the detector array to meet the desired processing capabilities for a viable sorting system may be described. Combining this information with the energy resolution and counting statistics requirement, one may determine the number of detectors, and thus the spatial resolution, required to adequately span the sensing area. Finally, a suitable communications data rate for transferring the spectra from each detector to the sorting computer at a targeted scan-rate may be used. This data rate may be significant and the coordination and transmission of the data may require a specialized, perhaps hardware, solution.

Single-pixel X-ray Detector.

A suitable off-the-shelf single pixel x-ray detector may be used in providing the spectra required to extract the data features identified.

The Data Reduction Techniques and Communications Interface Between Detector Array and Sorting Computer.

In one embodiment, a group of data-reduction operations to be done on the raw spectrum data at the detector array before the data is transferred to the sorting computer is provided. This group of data reduction operations may include object detection, variable spectral binning, summing of counts over selectable regions of interest, and peak estimation within regions-of-interest. The computing capabilities of the detector array may be determined by discussions with the vendor. The trade-offs between data reduction and detector array complexity may be balanced in consideration of maximum data transfer rate between detector and sorting computer, and by estimating the available computing power at the sorting computer.

According to one embodiment, the physical and logical interface used to transfer data from the detector array to the sorting computer is provided. The physical layer interface may be an industry standard such as PCI Express or another very high speed serial link. The logical interface may be selected to minimize the overhead required to receive the data at the sorting computer, e.g. the detector array may utilize Direct Memory Access (DMA) to place data directly into the sorting computer memory. A formal specification, including definitions for calibration, diagnostics, and other system verification tools, may be described.

Detector Array and Communications Interface.

According to one embodiment, the acquisition performance (in terms of spectral peak width and maximum count rate) and the communications interface (in terms of data delivery bandwidth) are described.

A Parallel System to Measure Transmissive X-ray Attenuation Running Simultaneously with XRF Peak Detection.

As earlier discussed, an x-ray transmission detector array can be utilized to measure x-ray attenuation on passing through a chip and this measurement used to estimate chip thickness for use in real-time calibration of fluorescence peak ratios which will vary depending upon chip thickness (for instance, for chips less than about 0.64 mm thickness the tin fluorescence peak will have a direct dependence upon chip thickness). Also an x-ray transmission detector array can be utilized to detect small dense inclusion (e.g., tungsten carbide pieces broken off tungsten carbide machining tool bits) which may be too small to fluoresce strongly enough for XRF detection. Additionally a dual energy x-ray transmission detector array can be utilized to find elemental absorption edges that fall between the two energy levels.

In an embodiment, the transmission detector arrays can be used for a small (6 inch) belt.

There may be benefits of using attenuation to calibrate the XRF peak detection results. A high speed digital interface to the transmission array may be provided. The sorting computer resources preferable to receive data simultaneously from the transmission and XRF arrays may be provided. Real-time sorting algorithms for transmission may be used. The configuration and user interface software used for both sensor types may be integrated. A matrix of titanium chips with tungsten inclusions or intermixed tungsten particles may be sorted.

Feature Extraction Algorithm and Computing Platform.

Software processes to receive spectrum data from the x-ray detector arrays and extract the features required for material sortation may be used. Any suitable computing power necessary to execute the algorithm and service all the detectors and ejectors in the system may be used. The technology may utilize system and real-time computing modules.

Hardware.

This hardware will include an infeed belt (or one or more gravity-fed channelized sliders), an x-ray source, an x-ray detector array, multiple single-pixel x-ray detectors, detector mounting hardware to position the detectors above or below the material stream, an x-ray collimation system, and an x-ray safe enclosure.

Real-time Feature Extraction and Sorting Decision Algorithm.

Any suitable sorting algorithm may be used. Examples may include but are not limited to "image match," "Vector analysis," and "Decision Tree" algorithms known to those skilled in the art.

In some embodiments, a flat conveyor belt is used for material presentation. In alternative embodiments, a channelized gravity-fed slider is used for material presentation. Other methods of feeding will be obvious to those skilled in the art.

Enclosure with Detector Array and X-ray Source.

The system may include suitable full-speed (full-width across belt or sliders) material presentation at the array of detectors. Fine-pitch ejector nozzles may be used. Paddle flippers and other ejector mechanisms may alternatively be deployed and are known by those skilled in the art. The x-ray source layout may provide uniform radiation across the detectors.

System Configuration and User Interface Software.

The system may utilize configuration and user interface software. This package includes applications to capture spectrum data, present the feature extraction results to the user, and allow parameter manipulation for optimizing the performance of the sorting algorithm.

Various non-limiting working examples are now described. In an embodiment, identification and removal of harmful contaminants in high-value scrap metal alloy machining chip streams is described to provide for "closed-loop" recycling opportunities. Specifically, it is desired to segregate a primarily titanium chip stream into "light" (e.g. tin free) and "heavy" (e.g. tin bearing or nickel bearing) fractions and remove other "foreign" materials such as tungsten from broken drill bits, which may have inadvertently contaminated the stream. The two titanium fractions may then be re-introduced to processing plants as viable feedstock. Sorting of Refractory Metals, Rare Earth Metals, and other materials such as mineral ores, glass, coal, plastics, and other matter may be processed similarly.

A description of the theoretical basis of alloy sortation is now described, but it should be appreciated is not limiting. A convenient demarcation for categorizing titanium chips into light and heavy groups is the presence of the element tin. The light group typically consists of "commercially pure" titanium Ti CP and the aluminum-vanadium alloy Ti 6-4. The heavy group consists of Ti 6-2-4-2, Ti 6-6-2 and Ti 17, with each alloy containing at least two percent tin. The approximate composition of each alloy, given as percentage by weight, is found in Table 4.

TABLE 4

Titanium Alloy Composition, Percentage by Weight.

| | Al | Ti | V | Cr | Zr | Mo | Sn |
|---|---|---|---|---|---|---|---|
| Ti CP | | 100 | | | | | |
| Ti 6-4 | 6 | 90 | 4 | | | | |
| Ti 6-2-4-2 | 6 | 86 | | | 4 | 2 | 2 |
| Ti 6-6-2 | 6 | 86 | 6 | | | | 2 |
| Ti 17 | 5 | 83 | | 4 | 2 | 4 | 2 |

Foreign materials, which are often found in a chip stream, are typically aerospace super-alloys and tungsten pieces. Super-alloy chips are introduced into the titanium stream by machining both metals in the same general vicinity and even machining the metals with the same device. Since many cutters are composed of tungsten carbide, fracturing of these bits during operation introduces tungsten into the stream. The approximate composition of three common super-alloys, given as percentage by weight, is found in Table 5.

TABLE 5

Super-Alloy Composition, Percentage by Weight.

| | Cr | Fe | Co | Ni | Nb | Mo |
|---|---|---|---|---|---|---|
| Inconel 706 | 16 | 39 | | 42 | 3 | |
| Inconel 718 | 19 | 23 | | 53 | 5 | |
| Waspaloy | 20 | 1 | 14 | 61 | | 4 |

Figure 8:
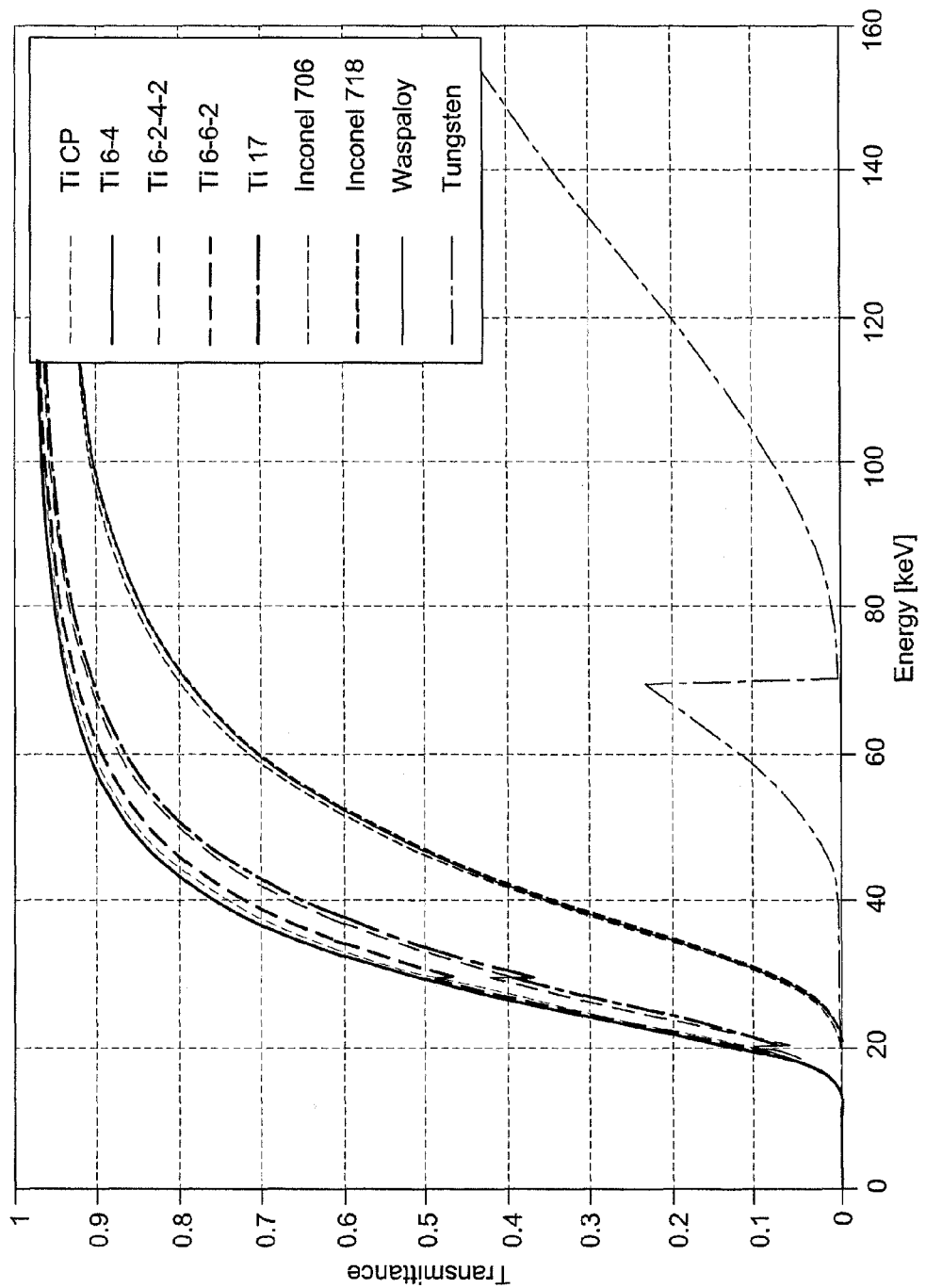
FIG. 8 shows the x-ray transmittance curves for various materials of interest at a nominal thickness of 0.3 mm.

To distinguish among the various material groups, consider the attenuation of x-rays as they pass through metal flakes. FIG. 8 shows the x-ray transmittance, defined as the ratio of transmitted to incident flux, curves for the materials of interests at a nominal thickness of 0.3 mm. From the figure, it can be seen that simply evaluating the attenuation around 80 keV provides ample information for distinguishing tungsten from the other materials. Furthermore, this assessment is sufficient for separating a 0.1 mm thick flake of tungsten from Waspaloy (a nickel-based superalloy) that is as thick as 2.5 mm.

Figure 9:
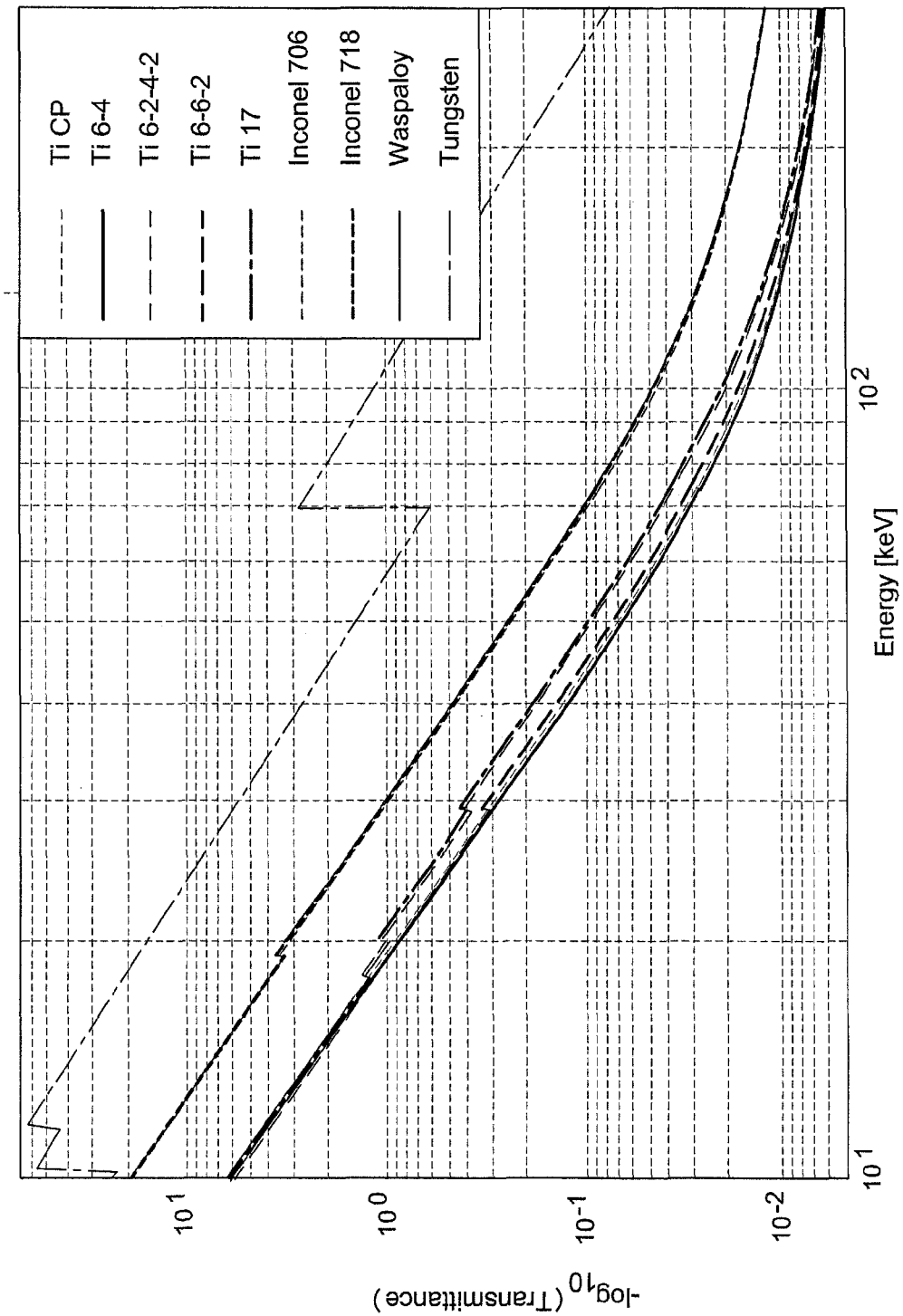
FIG. 9 shows the x-ray absorbance curves for various materials of interest, at a nominal thickness of 0.3 mm.

Attenuation may also be described through absorbance, which is defined mathematically as $-\log_{10}(\text{transmittance})$. This is a convenient characterization, since attenuation now becomes a linear function of thickness (i.e. doubling thickness exhibits a doubling of the absorbance value). FIG. 9 displays the absorbance curves for the various materials, again at a nominal thickness of 0.3 mm.

Figure 10:
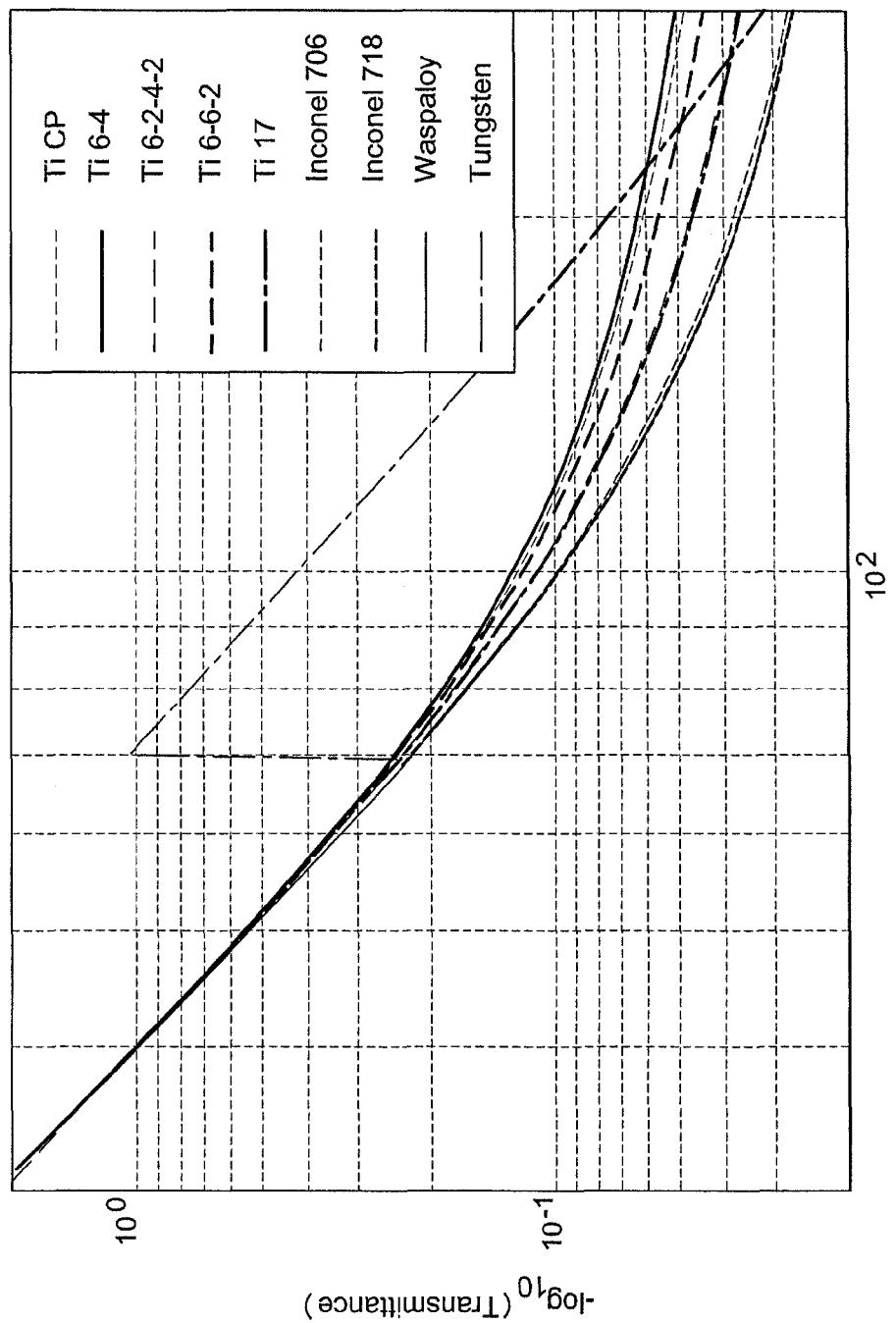
FIG. 10 depicts thickness-normalized curves for various materials, according to a non-limiting embodiment.

For separating the super-alloys from the titanium alloys, consider the energy region above 30 keV. Furthermore, consider a "thickness normalization" of the absorbance curves by scaling the 0.3 mm nominal thickness of each alloy so that the absorbance value at 40 keV is unity. The thickness-normalized curves for the materials are depicted in FIG. 10. Notice that curves of the titanium-based alloys tend to "flatten" more quickly at higher energies than do those of the nickel-based super-alloys. This phenomenon is the result of attenuation being dominated by x-ray scattering and may be used to differentiate between the two groups. In general terms, one may assess that the "steeper" the absorbance curve is at higher energies, the higher the "relative atomic number (Z)" of the alloy.

Figure 11:
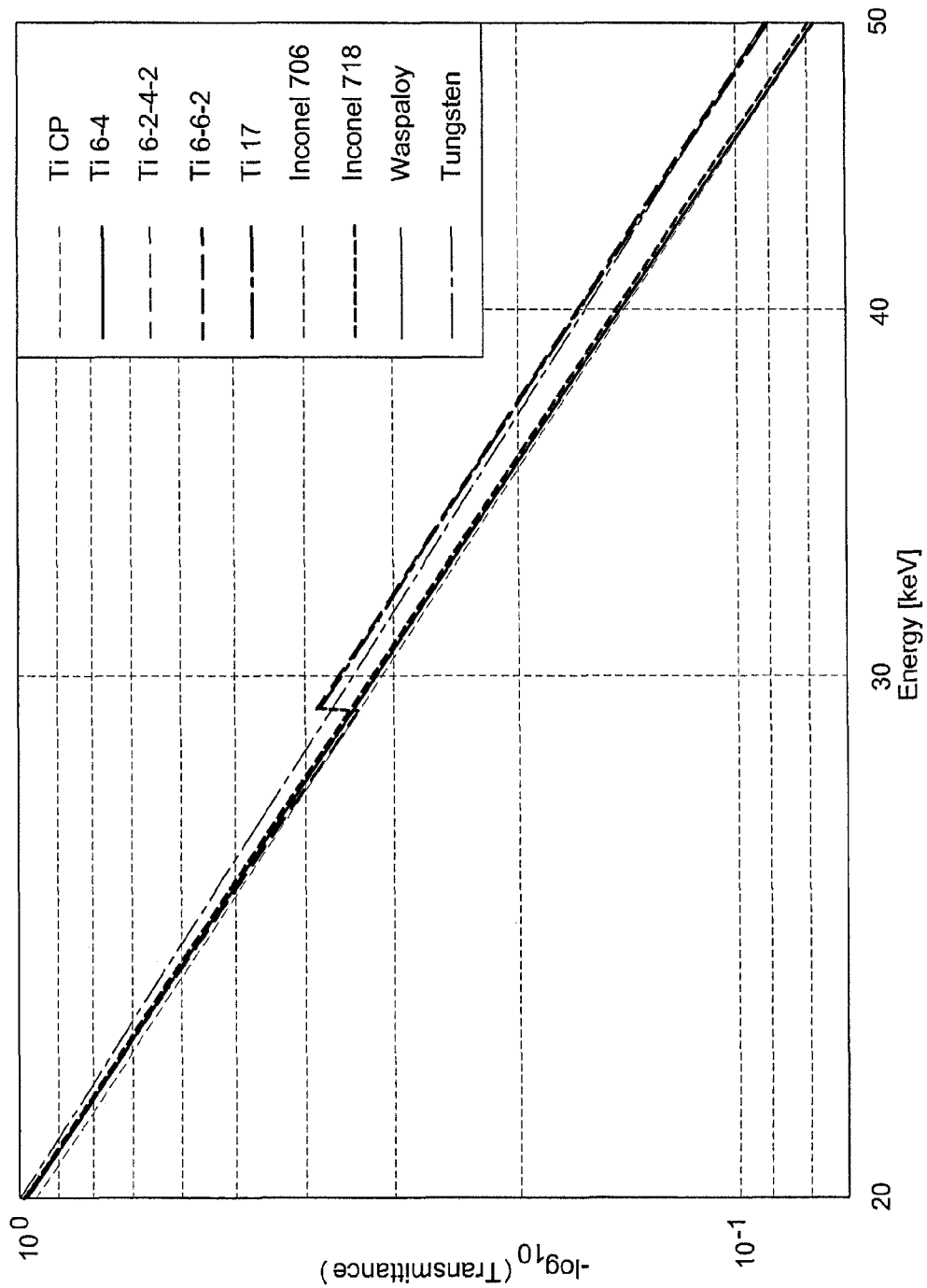
FIG. 11 shows thickness-normalized absorbance curves for various materials, according to a non-limiting embodiment.

For separation of titanium into the light and heavy groups, consider the thickness-normalized absorbance curves in the region of 20 to 50 keV as found in FIG. 11, which correspond to 20 keV. Notice that the most significant difference between the tin-laden alloys and other materials is the slight discontinuity at 29.2 keV. The discontinuity, or absorption edge, at this energy is unique to tin and due to attenuation being dominated by the photoelectric effect from impinging x-rays. It should also be noted that the amount of discontinuity is directly proportional to the relative percentage of tin in the alloy. Thus, an alloy with a higher concentration of tin would exhibit a greater discontinuity and amenability for robust separation.

Figure 12:
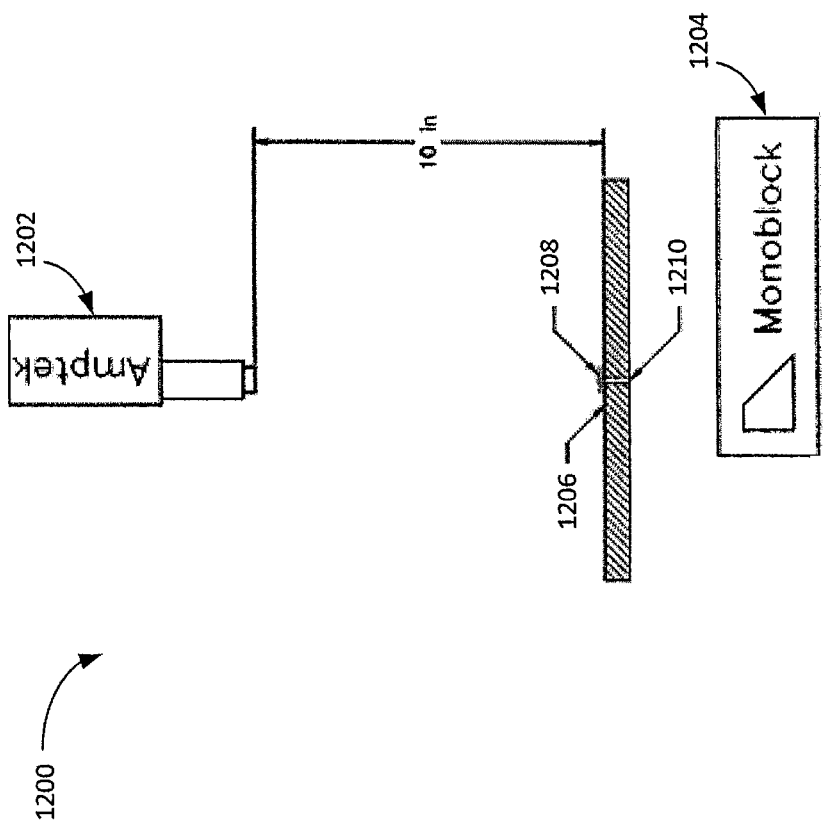
FIG. 12 illustrates a physical arrangement for acquiring various x-ray spectra from materials of interest, according to a non-limiting embodiment.

Now described is some empirical validation of alloy sortation using techniques described herein. According to one aspect, methods of separation may involve analyzing empirical transmission spectra. To acquire the x-ray spectra, a XR-100T-CZT model detector from Amptek and a 480 W Monoblock x-ray system from Spellman may be utilized. The physical arrangement 1200 for acquiring the various spectra is represented in FIG. 12.

Separation of Ti-6-4 from Tin-Bearing Titanium (Ti-17)

Empirical transmission spectra may be analyzed. To acquire the x-ray spectra, a XR-100T-CZT model detector 1202 from Amptek and a 480 W Monoblock x-ray system 1204 from Spellman may be used. The physical arrangement 1200 may include a lead plate, such as lead plate 1206 configured to hold a test flake 1208. In some embodiments, the lead plate may have a thickness of ½ inches, or any suitable thickness. There may also be a hole for collimation, such as hole 1210. In some embodiments, the width of the hole 1210 may be ⅛ inches, thought the present disclosure is not limited in this regard.

Figure 13:
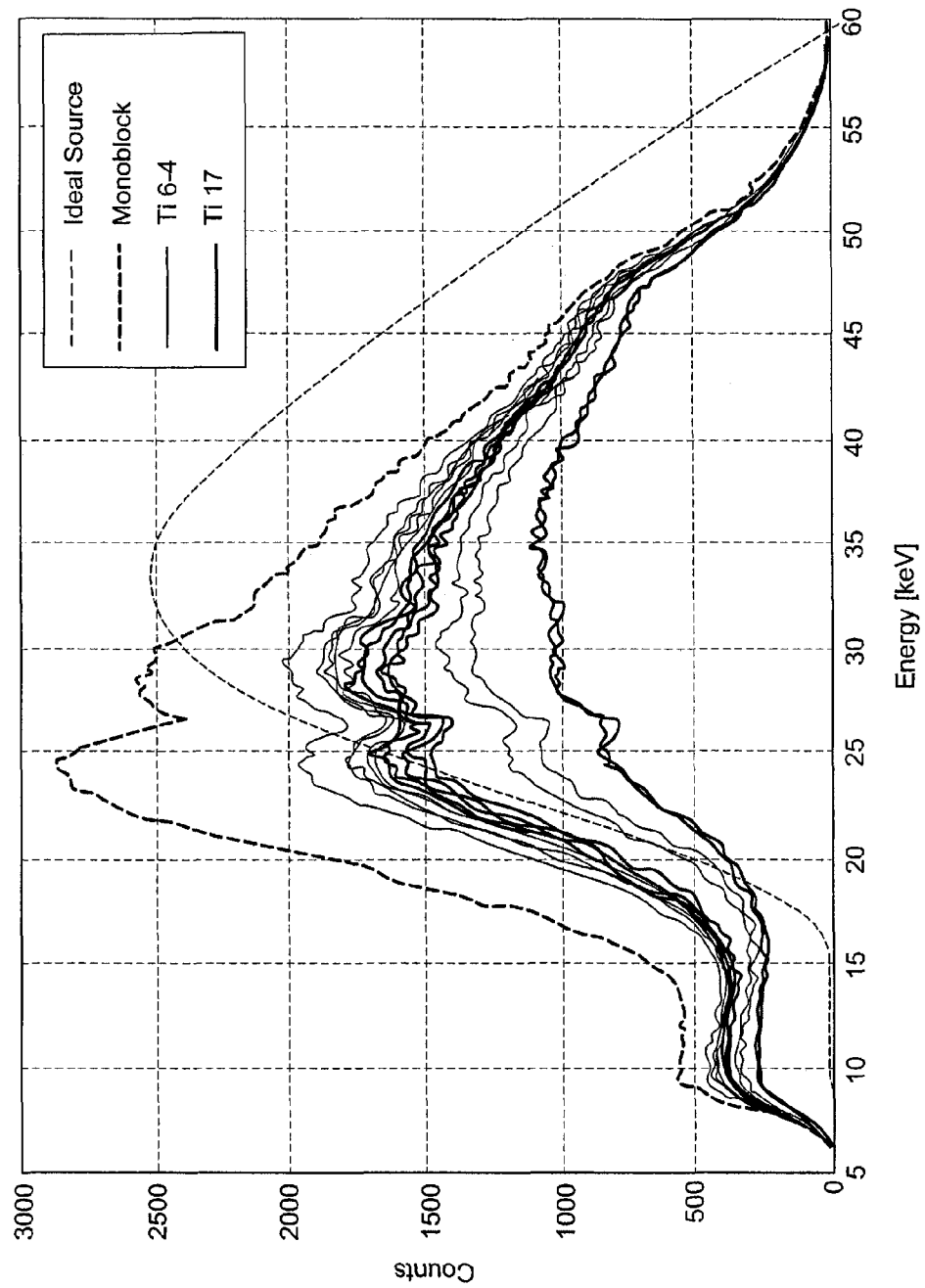
FIG. 13 displays "low energy" x-ray spectra, according to a non-limiting embodiment.

FIG. 13 displays "low energy" x-ray spectra for an ideal x-ray tube operating at 60 keV, the Monoblock source and 7 metal chips each of Ti 6-4 and Ti 17, with a thickness of between 0.3 and 0.6 mm. An observation in FIG. 13 is that the acquired Monoblock spectrum appears "shifted" from its ideal spectrum, which may be due to x-ray scattering from the lead orifice used in collimation. Consider, for example, when a 40 keV x-ray leaves the tube window and strikes the collimator: some of its energy may be lost in inelastic collisions and thus registered by the detector as a lower energy x-ray. This scattering process also helps explain the "plateau" seen between 10 and 15 keV, since these energies should be significantly absorbed by the tube window.

Figure 14:
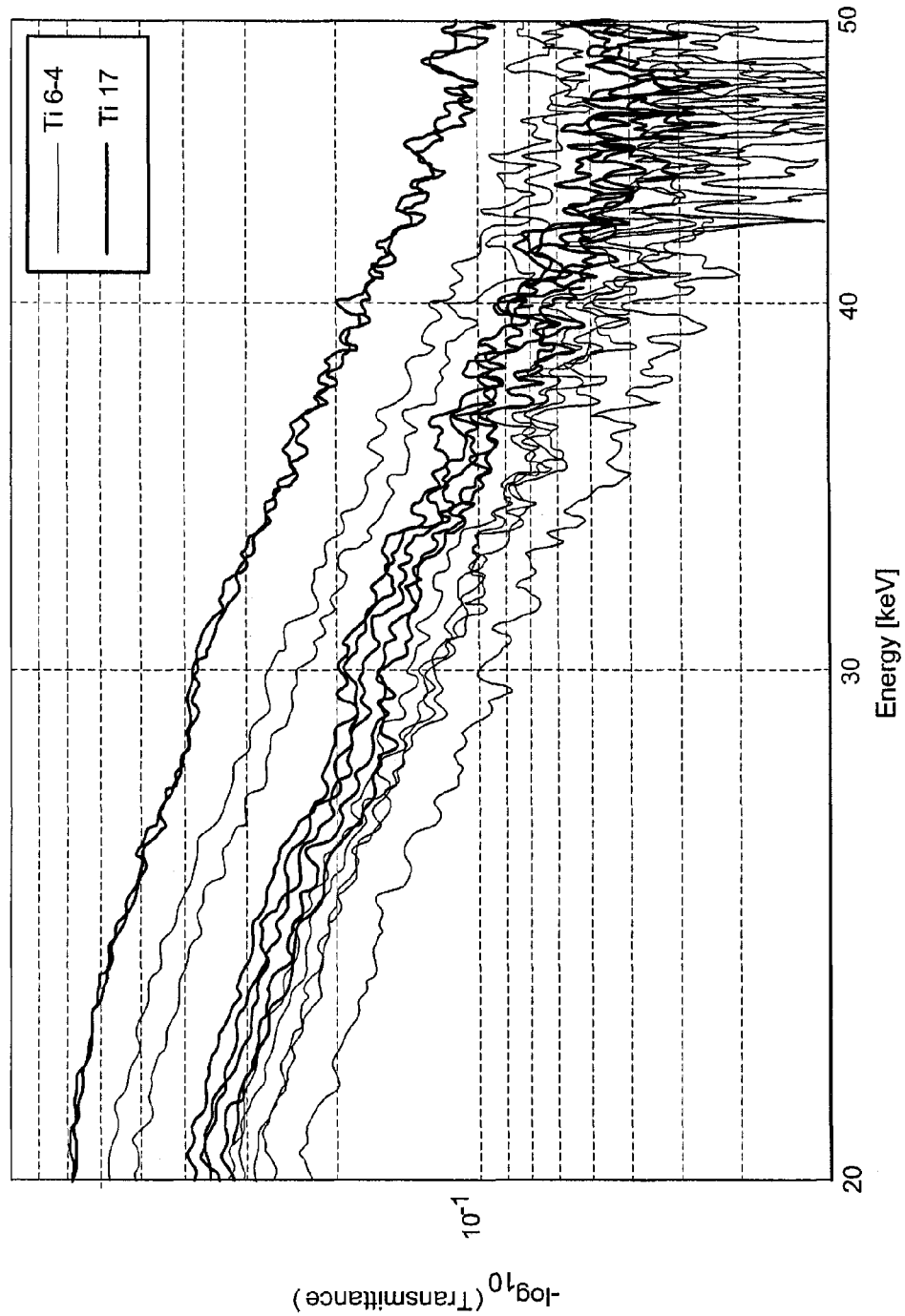
FIG. 14 shows Ti 6-4 and Ti 17 absorbance curves, according to a non-limiting embodiment.

The results of numerically computing the absorbance curves for the flakes of FIG. 13 are seen in FIG. 14, such that FIG. 14 shows Ti 6-4 and Ti 17 absorbance curves. Energies below 20 keV were excluded due to excessive distortion from scattering, while energies above 50 keV were excluded due to excessive distortion from a diminished signal-to-noise ratio. Furthermore, this energy range affords a direct visual comparison to curves in FIG. 11. Notice, that while the absorption edge of Ti 17 is not nearly as pronounced in the data as that of the model, a slight "bump" is visible.

One technique to elicit the amount of discontinuity for these absorbance curves would be to approximate the data both below and above the absorption edge by first-order polynomials with equal slopes and inspect the offset difference. However, since the NEXIS system only provides 5 energy ranges for sampling a spectrum, as compared to the 1024 ranges (bins) of the Amptek detector, detecting discontinuities from first-order (or higher) polynomial approximations is not feasible with this particular non-limiting setup.

To detect the absorption edge of tin with only five consecutive regions of interest (ROIs), consider the entire spectral regions of 22.0 to 27.5 keV and 30.7 to 38.0 keV. For these spans, the value associated with each ROI is the integral of the spectrum between the limits. Thus, we can form an approximation to the transmittance as $$T_O(e_0,e_1) = \int_{e_0}^{e_1} S_O(e)/\int_{e_0}^{e_1} S_I(e),$$

where $e_0$ and $e_1$ are the ROI limits, $S_I$ is the incident spectrum and $S_O$ is the transmitted spectrum.

Figure 15:
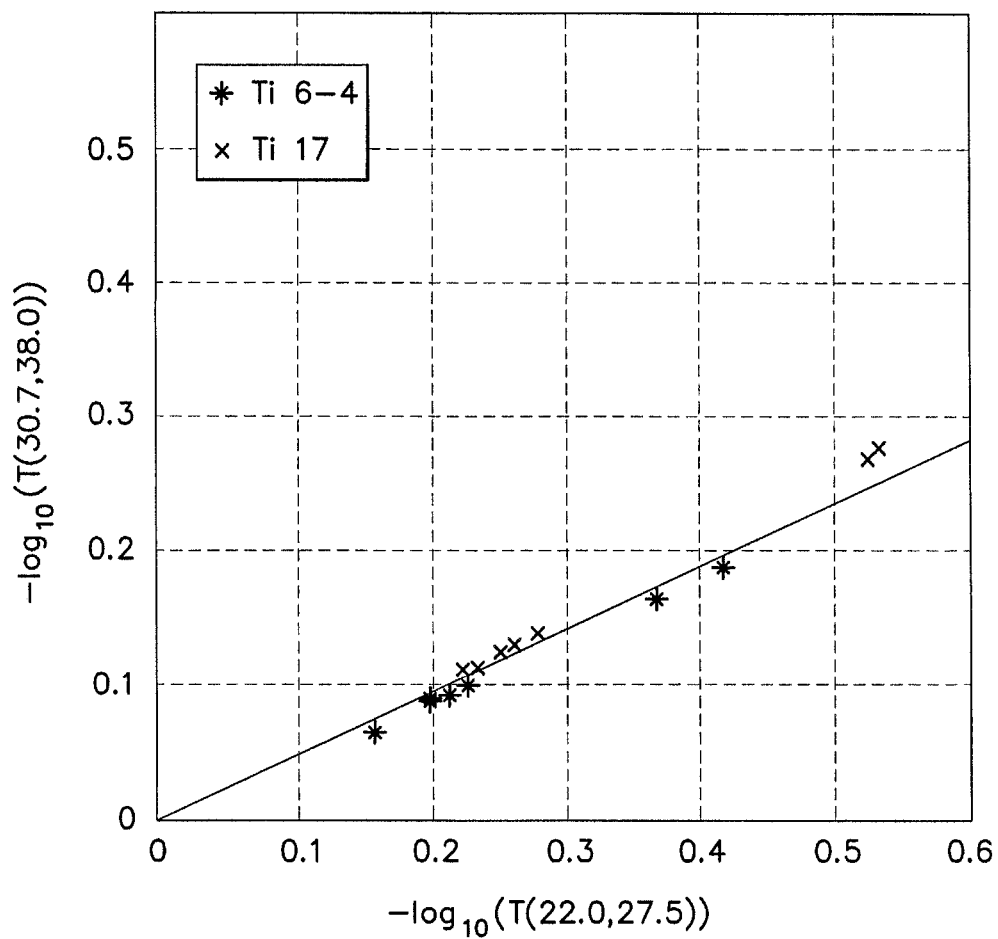
FIG. 15 shows approximated absorbance values of metal flakes, according to a non-limiting embodiment.

Similarly, an approximation to the absorbance can be formed by computing $-\log_{10}(T_O)$. FIG. 15 shows the approximated absorbance values of the metal flake (Ti 6-4 and Ti 17) over the ROIs. An included discrimination line demonstrates a slight, but clear, separation between the two groups. Therefore, the empirical data from an Amptek detector indicates that utilizing the absorption edge of tin to distinguish between "light" and "heavy" titanium alloys is feasible, and thus is performed according to one embodiment.

Separation of Titanium Alloys from Superalloys

Figure 16:
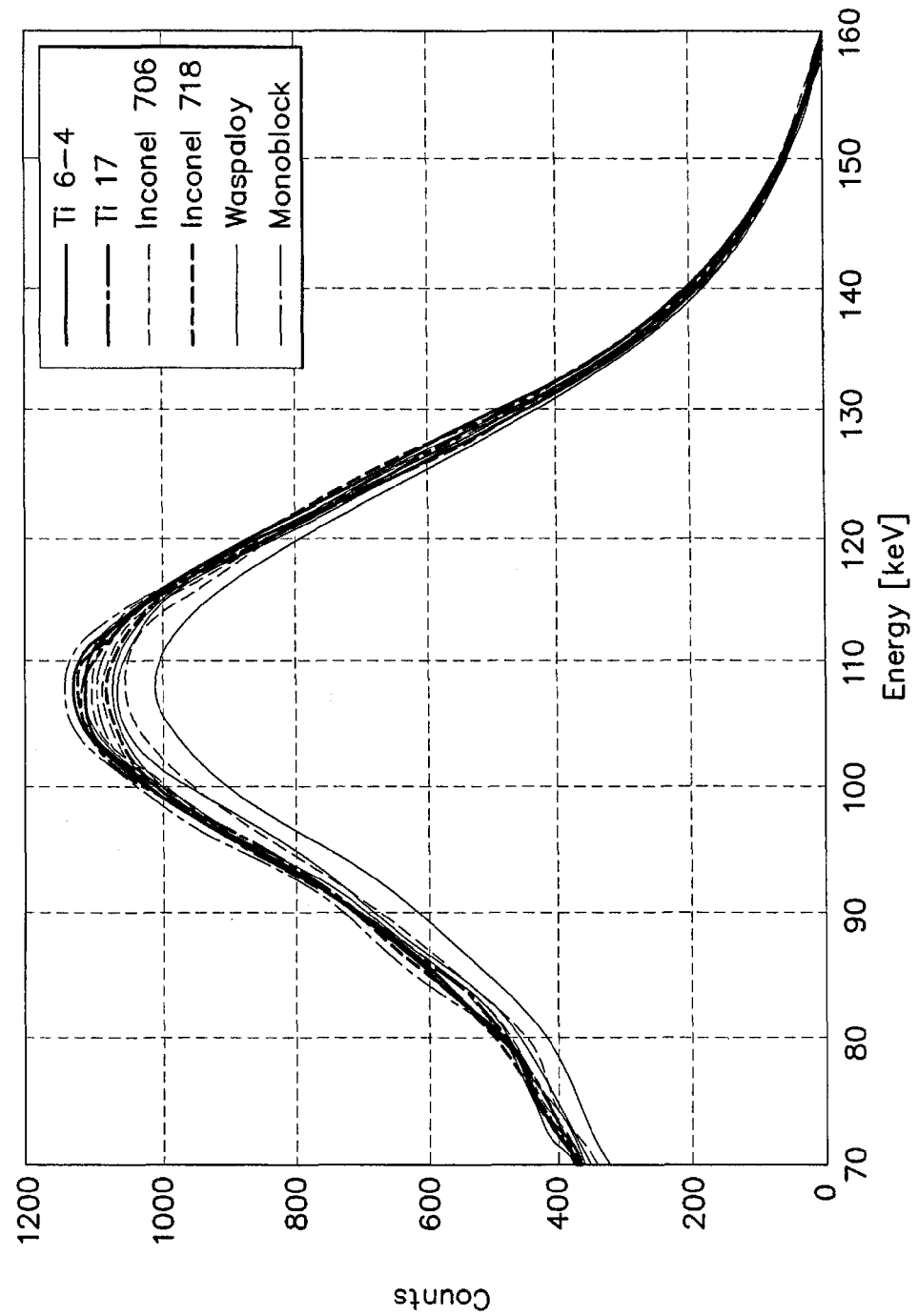
FIG. 16 displays "high energy" x-ray spectra, according to a non-limiting embodiment.

According to one embodiment, separation of titanium alloys from super-alloys based on their "relative Z" is performed. FIG. 16 displays the "high energy" x-ray spectra of multiple chips of the various materials (three chips from each alloy composition), with a thickness of between 0.3 and 0.7 mm. The Monoblock spectrum was filtered with a ⅝ inch bar of copper to produce the energy peak near 110 keV. As before, the XR-100T-CZT model detector from Amptek was used in these tests.

Figure 17:
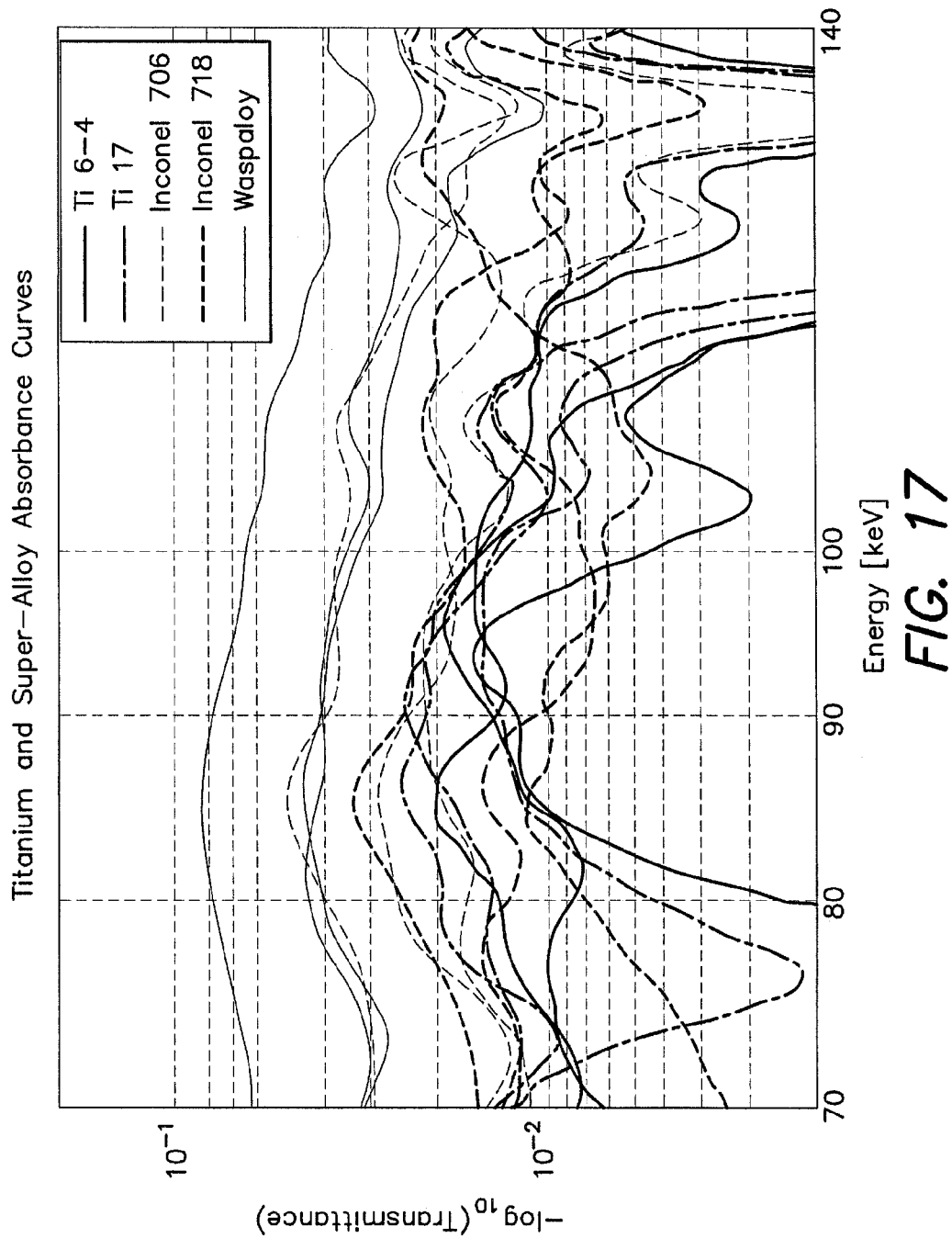
FIG. 17 shows Titanium and Super-Alloy absorbance curves, according to a non-limiting embodiment.

We can again numerically compute the absorbance for these flakes and display the resulting curves in FIG. 17, which show titanium and superalloy absorbance curves. There appears to be little similarity between these curves and the model curves found in FIG. 9. However, the upper-most curve of a Waspaloy flake provides a clue for the discrepancies, since it bears the closest resemblance to the model. This flake was the thickest of all flakes at 0.7 mm. According to the model, the transmittance at 100 keV should be 80%[†], yet the data indicates a value of 89% (nearly 50% error). Similarly, for a 0.3 mm thick flake of Ti 6-4, the transmittance at 100 keV should be 97% but is approximately 98.5%. Since the x-rays are only slightly attenuated by these "thin" flakes, noise tends to mask the underlying signal and prevent robust separation.

[†] At 100 keV, the 0.3 mm Waspaloy flake model shows an absorbance of $4.2 \times 10^{-2}$ or transmittance of $10^{-0.042} \approx 90\%$. Similarly, a 0.7 mm flake exhibits an absorbance of $(0.7/0.3) * 4.2 \times 10^{-2}$ or transmittance of $10^{-0.098} \approx 80\%$.

Ensuring the feasibility of separating titanium alloys from super-alloys based on their "relative Z" may require in some non-limiting instances changing some combination of three characteristics: acquisition noise, x-ray energy regions and material thickness. Acquisition noise can be reduced by increasing acquisition times. However, for high-speed sortation, a sufficient increase in acquisition time is probably not practical. Inspection of FIG. 10 reveals that at the 300 keV point, there is a greater difference between alloy groups than at the 160 keV limit imposed by the Monoblock maximum energy range. However, at the 300 keV point, the thickness of a flake would need to be greater than 2.5 mm to improve the signal to noise ratio.

Example of Implementation of Alloy Sortation

Figure 18:
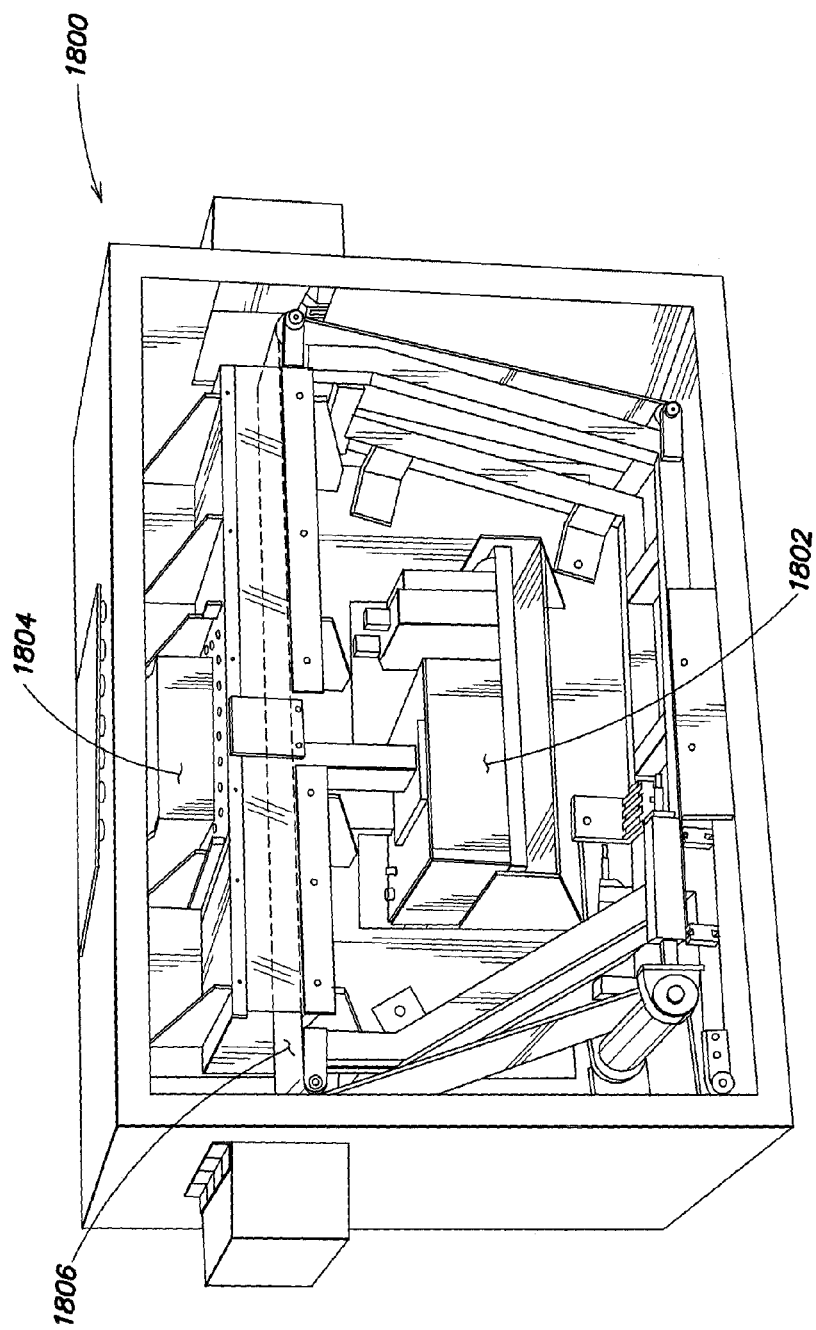
FIG. 18 is a schematic of a sortation system comprising a Monoblock x-ray module, the NEXIS detection module and a conveyor, according to a non-limiting embodiment.
Figure 19:
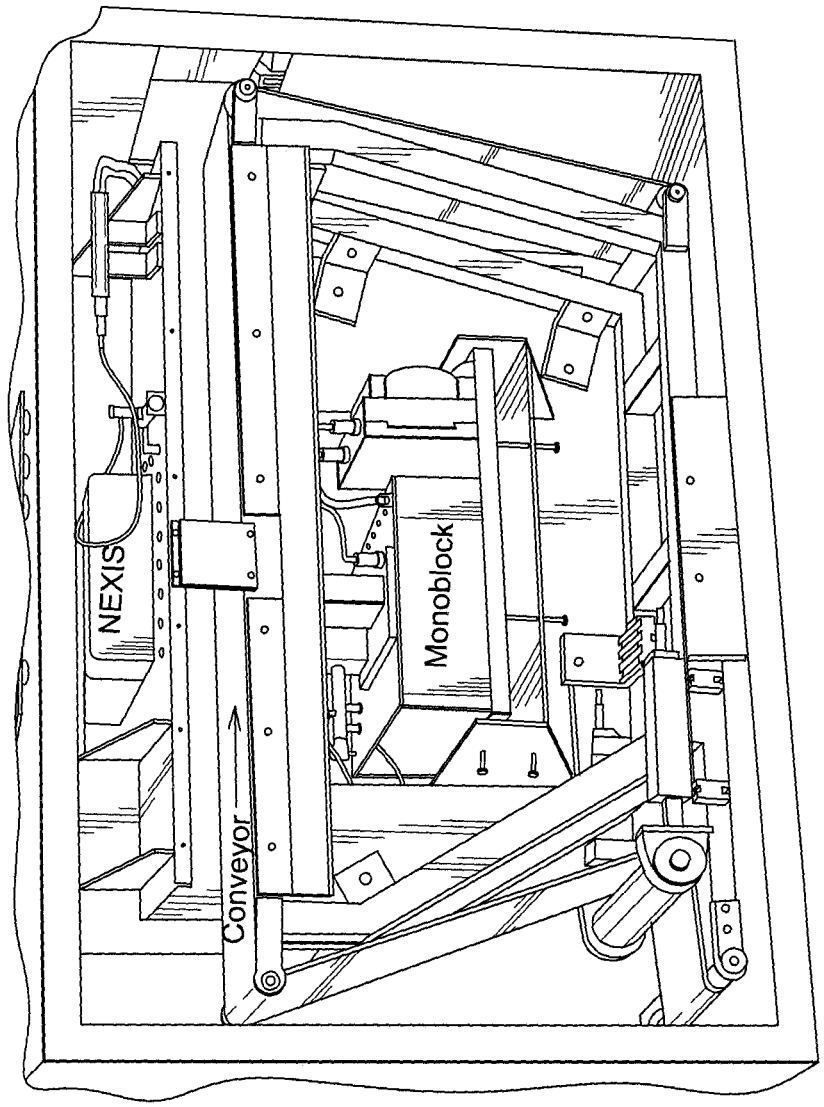
FIG. 19 is a photograph of a sortation system comprising a Monoblock x-ray module, the NEXIS detection module and a conveyor, according to a non-limiting embodiment.

According to one non-limiting embodiment shown in the schematic of FIG. 18, a sortation system 1800 comprises a Monoblock x-ray module 1802, the NEXIS detection module 1804 and a conveyor 1806. A photograph of the system 1800 is shown in FIG. 19.

In the sortation system 1800 shown in FIG. 18, the NEXIS system 1802 comprises eight sets of CZT (Cadmium Zinc Telluride) crystal detectors, where each set is pixilated into thirty-two individual detectors. The physical layout of the thirty-two detectors is arranged as two columns with sixteen detectors in each column. Since the 8 sets of detectors are serially abutted in column-wise fashion, the detection system provides 2 columns of 128 detectors. Thus, each column can produce a 128-by-N image, where N is an arbitrary number of frames. Furthermore, since the supporting electronics is capable of measuring five consecutive ROIs, each "pixel" in the 128-by-N image is represented by a five-element vector.

Each set of thirty-two detectors is assigned to a corresponding XENA (X-ray ENergy-binning Applications) chip for processing. The XENA chip provides thirty-four (thirty-two detector and two test) "channels" which operate in parallel to condition the detector signal and count x-ray events. Signal conditioning includes shaping and applying a gain and an offset. Once the signal is properly conditioned, five analog comparators and counters record signal transitions as x-ray events.

Figure 20:
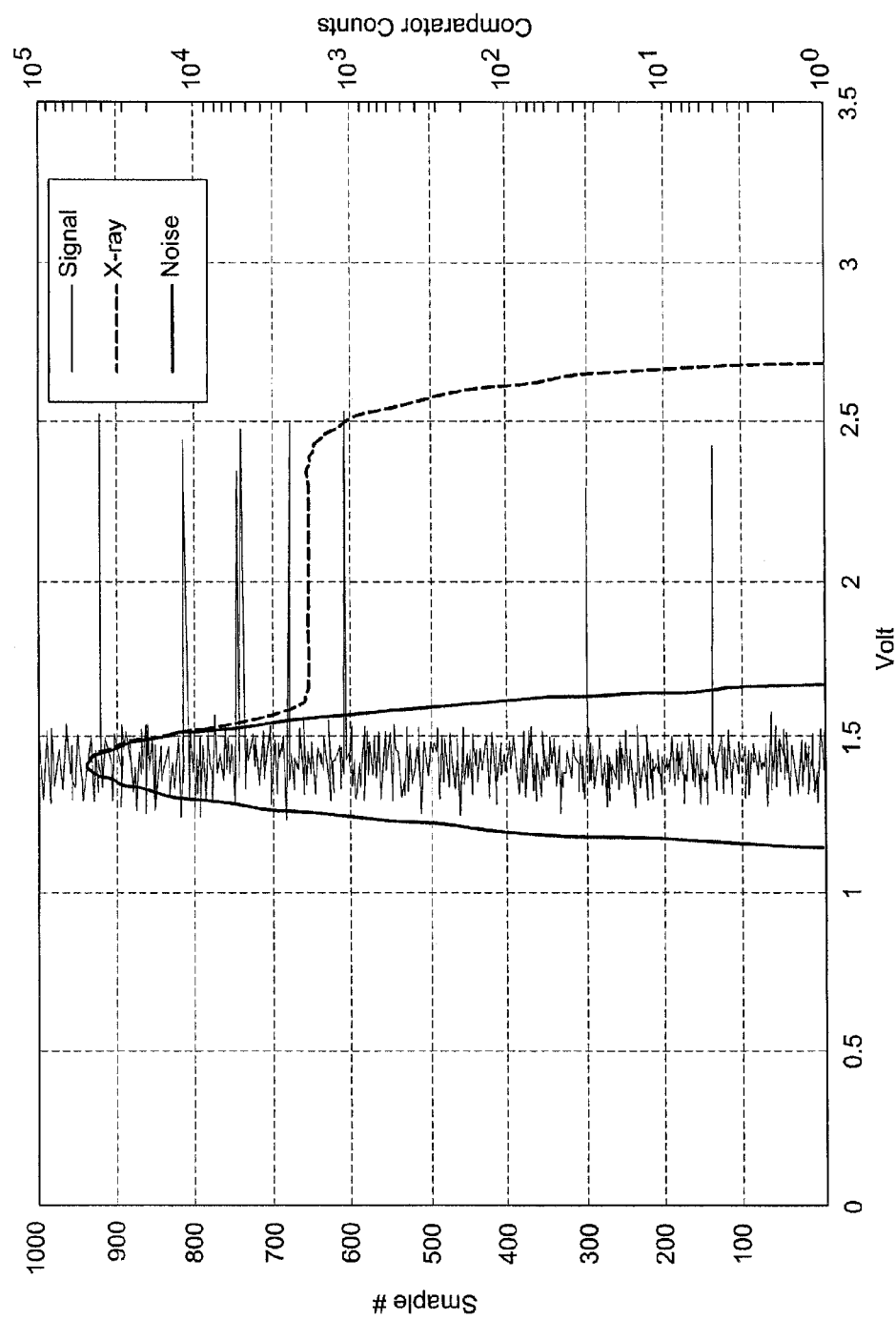
FIG. 20 illustrates a simulated detector signal, according to a non-limiting embodiment.

To better comprehend the behavior of a channel when exposed to incident x-rays, consider a simulation. FIG. 20 illustrates a simulated detector signal. Suppose that when no x-rays are present, the detector signal is a nominal 1.4 volts. Furthermore, when monochromatic x-rays equivalent to 1.1 volts are present, the detector signal is a nominal 2.5 volts.

The "red" graph in FIG. 20 depicts $1 \times 10^3$ (of $2 \times 10^5$) samples of this detector signal which is composed of noise and 9 (of $2 \times 10^3$) x-ray events.

To count the perceived x-ray events, one may "sweep" the comparator threshold value from 0 to 3.5 volts. Since the smallest signal voltage remains above about 1.15 volts, a sweep of the comparator threshold from 0 to 1.15 volts reveals no signal transitions across the threshold and thus no counts are accumulated. As one continues the sweep towards 1.4 volts, the number of transitions increases and finally reaches a peak. The traces of FIG. 20 indicate the perceived events at a given threshold voltage for the detector signal with x-rays ("X-ray") and the detector signal without x-rays ("Noise"). Notice that the value for the x-ray trace is $2 \times 10^3$ between 1.65 and 2.3 volts and accurately indicates the number of "true" x-ray events.

Figure 21:
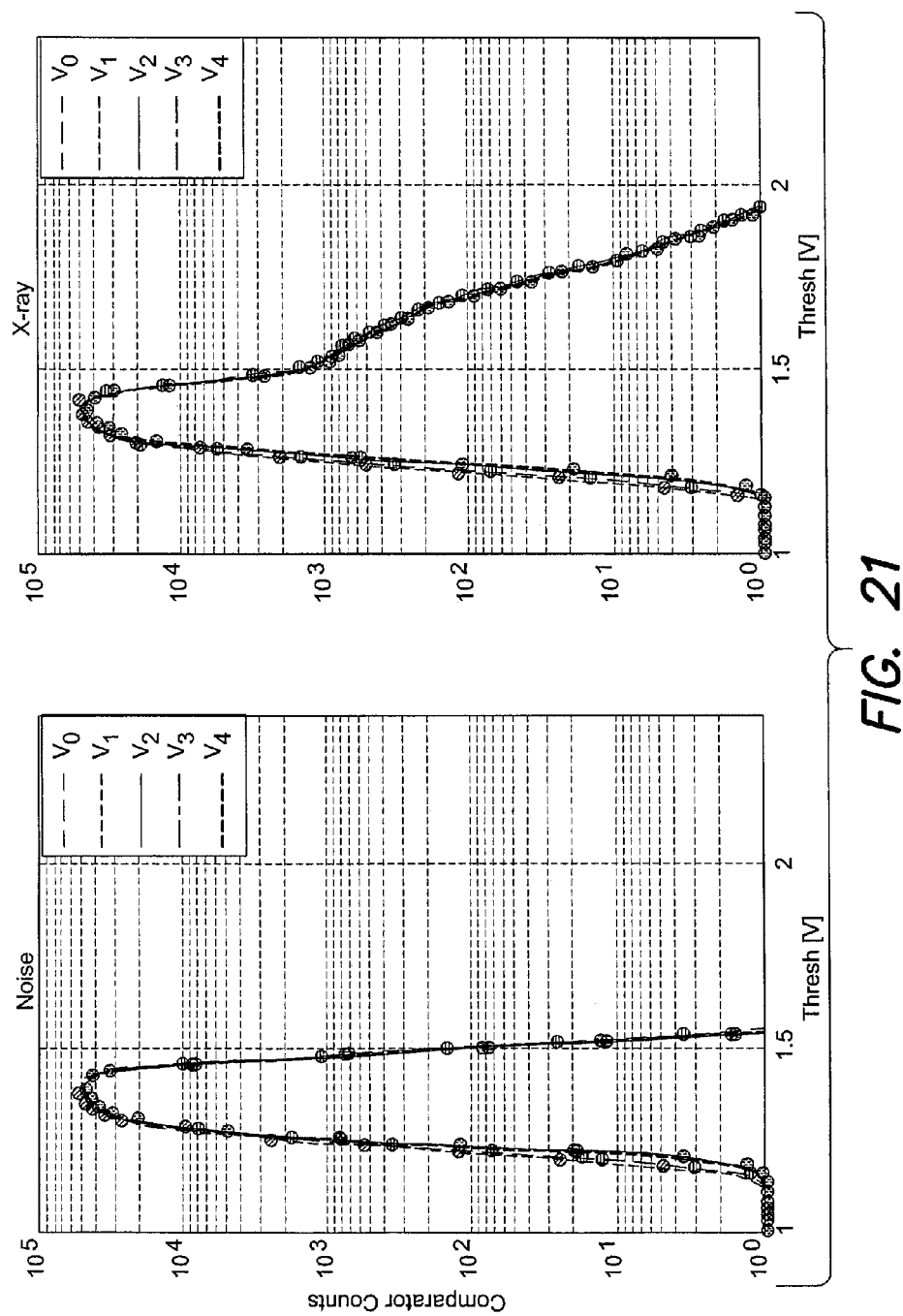
FIG. 21 displays detection results, according to a non-limiting embodiment.

FIG. 21 displays the results of sweeping the thresholds of all five comparators associated with an arbitrary detector (Chip 3, Channel 20) from 1.0 to 2.4 volts. The left-hand graph is produced when no x-rays are present, and the right-hand graph shows the results of setting the Monoblock to 60 keV. It can be seen that the noise peaks around 1.4 volts, and that "true" x-rays events begin to dominate the signal near 1.5 volts. Furthermore, since no significant events are seen above 1.95 volts, it is concluded that a 60 keV x-ray induces an approximate 0.55 volt change in the detector signal.

Figure 22:
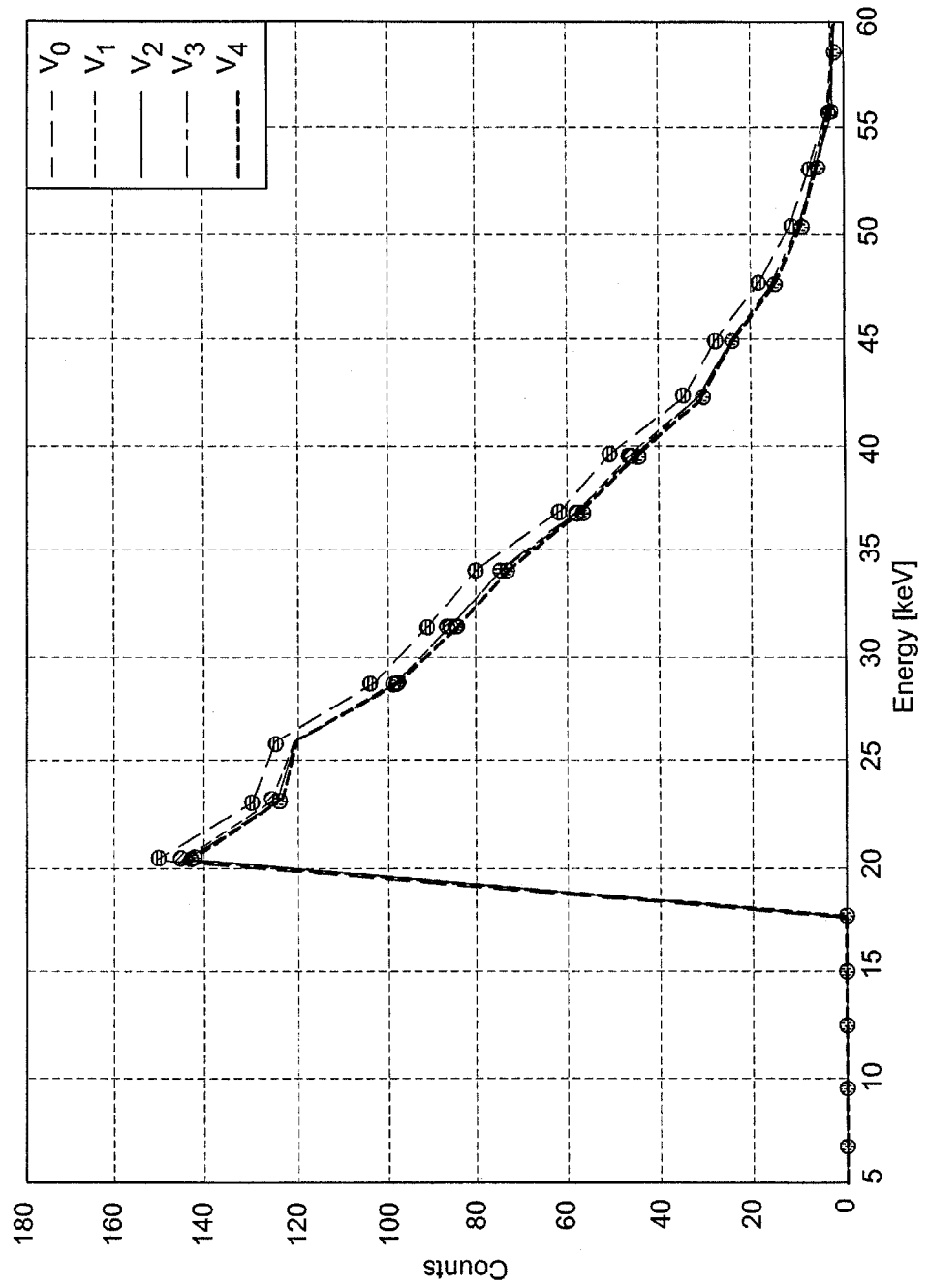
FIG. 22 shows an x-ray spectrum as measured by one detector in a NEXIS system, according to a non-limiting embodiment.

The underlying x-ray spectrum may be generated from the curve of "comparator counts" by numerical differentiation followed by subtraction of the "noise" from the "x-ray" spectrum. FIG. 22 shows this x-ray spectrum as measured by one detector in the NEXIS system. While the lower energies have been truncated below a signal-to-noise ratio of 20, a comparison with the Monoblock spectrum in FIG. 13 reveals that the NEXIS system is considerably more noisy than the Amptek detector.

To test whether the NEXIS system can distinguish between the two titanium alloys, four detectors where chosen to analyze four flakes each of Ti 6-4 and Ti 17. Since calibration among the channels is not very precise, the boundaries of two ROIs where optimized for each channel and resulted in an average range of 23.6 to 29.0 keV and 33.8 to 38.6 keV. Counts for each ROI were composed by averaging 25 acquisitions at 10 m-sec each. For the entire acquisition time of 250 m-sec, approximately $20 \times 10^3$ total x-ray events were detected.

Figure 23:
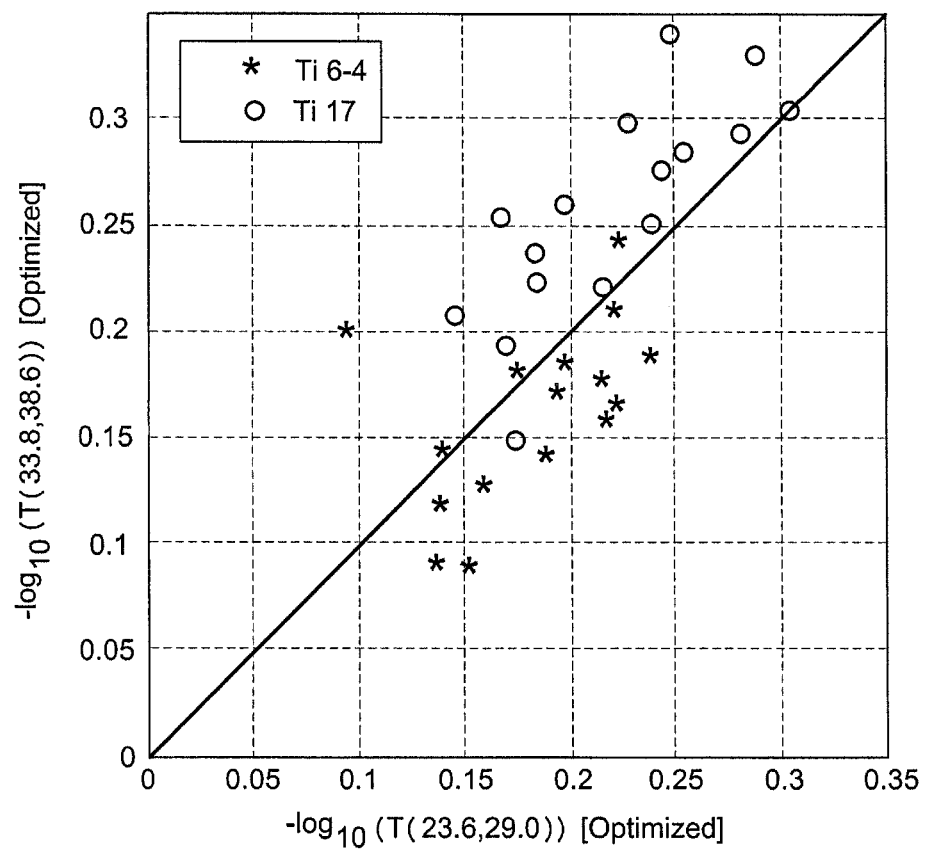
FIG. 23 shows the results of analyzing multiple titanium samples, according to a non-limiting embodiment.

FIG. 23 shows the results of analyzing the thirty-two titanium samples. It is evident from this figure that the two alloys are separable.

Conclusion

Various aspects and embodiments have been described for identifying and removing harmful contaminants in high-value scrap metal alloy machining chip streams to provide recycling opportunities. In some embodiments, segregation of a primarily titanium chip stream into "light" and "heavy" fractions and removal of other "foreign" materials which may have inadvertently contaminated the stream is performed. Multiple methods were described for meeting these goals. One method distinguishes between the titanium fractions, while another method exposes foreign materials. Alternatives are also possible.

In non-limiting working examples, the titanium alloys were seen to be reliably separable when using an Amptek x-ray detection system.

In some non-limiting embodiments, separation of super-alloys from titanium alloys may be performed for materials thicker than 2.5 mm.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, some of the embodiments may be implemented using hardware, software or a combination thereof. When implemented in software, the software code can be executed on any suitable processor or collection of processors, whether provided in a single computer or distributed among multiple computers.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. In some embodiments, computer readable media may be non-transitory media.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In addition, while some references have been incorporated herein by reference, it should be appreciated that the present application controls to the extent the incorporated references are contrary to what is described herein.

The invention claimed is:

1. A material sorting system, comprising:
a conveyor configured to convey pieces of metal;
an x-ray source configured to irradiate one or more of the pieces of metal with incident x-rays as they are conveyed by the conveyor to generate fluoresced x-rays from the one or more pieces of metal and transmitted x-rays transmitted through the one or more pieces of metal;
an x-ray fluorescence detector array configured to detect the fluoresced x-rays and produce x-ray fluorescence data for at least a first piece of metal of the one or more pieces of metal;
an x-ray transmission detector configured to detect the transmitted x-rays and produce x-ray transmission data for at least the first piece of metal; and
at least one processor configured to:
obtain data for a plurality of characteristic x-ray fluorescence peaks;
identify a plurality of peaks of the x-ray fluorescence data as corresponding to respective ones of the characteristic x-ray fluorescence peaks;
determine, using the peak identification, the presence of a plurality of materials in the first piece of metal;
obtain data for a plurality of predetermined sorting categories, at least two of the sorting categories being associated with one or more materials; and
identify at least one sorting category for the first piece of metal based at least in part on the x-ray transmission data and by comparing the determined plurality of materials in the first piece of metal with the sorting categories.

2. The material sorting system of claim 1, wherein the at least one processor is further configured to:
receive the x-ray fluorescence data and the x-ray transmission data;
determine thickness data for one or more of the pieces of metal based at least in part on the x-ray transmission data; and combine the thickness data with the x-ray fluorescence data to determine at least a partial composition of one or more of the pieces of metal.

3. The material sorting system of claim 2, wherein the x-ray transmission data comprises data about two or more energy levels, and wherein the at least one processor is configured to determine the thickness data at least in part by comparison of the x-ray transmission data of the two or more energy levels.

4. The material sorting system of claim 1, wherein the x-ray fluorescence detector array comprises an array of x-ray fluorescence detectors configured to detect fluoresced x-rays from pieces of metal disposed on different parts of the conveyor.

5. The material sorting system of claim 4, wherein the array of x-ray fluorescence detectors is arranged substantially across a width of the conveyor.

6. The material sorting system of claim 1, wherein the x-ray transmission detector is a single pixel x-ray transmission detector.

7. The material sorting system of claim 1, wherein the x-ray fluorescence detector array comprises two rows of x-ray fluorescence detectors.

8. The material sorting system of claim 7, wherein the two rows are adjacent.

9. The material sorting system of claim 7, wherein the two rows are staggered.

10. The material sorting system of claim 7, wherein the two rows are parallel.

11. The material sorting system of claim 7, wherein at least one of the x-ray fluorescence detectors is larger than ½ inch in size.

12. The material sorting system of claim 7, wherein at least one of the x-ray fluorescence detectors is smaller than 10 mm in size.

13. The material sorting system of claim 1, wherein the conveyor includes one or more openings.

14. The material sorting system of claim 1, wherein the conveyor comprises one or more mesh sections.

15. The material sorting system of claim 1, wherein the conveyor comprises two conveyors configured to convey the one or more pieces of metal into and out of an irradiation zone in which the x-ray source is configured to irradiate the one or more pieces of metal with the incident x-rays.

16. The material sorting system of claim 15, wherein the two conveyors are configured in parallel with a gap between them.

17. The material sorting system of claim 15, wherein the two conveyors are configured in series.

18. The material sorting system of claim 1, wherein the conveyor comprises a vibrating feeder.

19. The material sorting system of claim 1, wherein the x-ray fluorescence data and/or x-ray transmission data form at least one spectrum at or about one or more energy levels.

20. The material sorting system of claim 19, wherein the at least one processor is configured to process the spectrum.

21. The material sorting system of claim 20, wherein the at least one processor is configured to perform resultant vector analysis of the spectrum and/or decision tree processing.

22. The material sorting system of claim 19, wherein the at least one processor comprises a sorting computer with real-time processing capability, where the computer includes an isolated partition dedicated to the sorting task.

23. The material sorting system of claim 1, wherein the sorting system is configured to separate titanium alloys from superalloys.

24. The material sorting system of claim 1, wherein the sorting system is configured to separate a first titanium alloy from a second titanium alloy.

25. The material sorting system of claim 24, wherein the first titanium alloy comprises tin and wherein the second titanium alloy does not.

26. The material sorting system of claim 1, wherein the sorting system is configured to separate a first superalloy from a second superalloy.

27. The material sorting system of claim 1, wherein the x-ray fluorescence detector array is configured at approximately 45 degrees from a direction at which the x-ray source irradiates the one or more pieces of metal.

28. The material sorting system of claim 1, wherein the one or more pieces of metal have thicknesses up to approximately 5 mm.

29. The material sorting system of claim 28, wherein the one or more pieces of metal comprise titanium.

30. The material sorting system of claim 1, further comprising an ejector configured to selectively direct the one or more pieces of metal after they are irradiated with the incident x-rays.

31. The material sorting system of claim 30, wherein the ejector comprises an air ejector.

32. The material sorting system of claim 30, wherein the ejector comprises a paddle ejector.

33. The material sorting system of claim 1, wherein the x-ray transmission detector and/or x-ray fluorescence detector array comprises one or more detectors selected from the group consisting of: Cadmium Telluride (CdT), Cadmium Zinc Telluride (CZT), lithium drifted silicon (SiLi) and Silicon Drift (SDD) detectors.

34. The material sorting system of claim 1, wherein the x-ray transmission detector is configured to produce an x-ray image of at least one piece of the one or more pieces of metal.

35. The material sorting system of claim 1, wherein the material sorting system is configured to sort the one or more pieces of metal based at least in part on an effective Z (Zeff) of the pieces using the x-ray transmission data.

36. The material sorting system of claim 1, wherein the one or more pieces of metal comprise alloys and wherein the material sorting system is configured to sort the alloys.

37. The material sorting system of claim 36, wherein the one or more pieces of metal represent machining chips.

38. The material sorting system of claim 1, wherein the system is used to remove inclusions of refractory metals from titanium.

39. The material sorting system of claim 1, wherein the one or more pieces of metal comprise glass, and wherein the material sorting system is configured to sort the glass.

40. The material sorting system of claim 1, wherein the one or more pieces of metal comprise mineral ores and wherein the material sorting system is configured to sort the mineral ores.

41. The material sorting system of claim 1, wherein sortation of the one or more pieces of metal is accomplished by operating the material sorting system in a fully automated manner.

42. The material sorting system of claim 1, wherein the at least one processor is configured to process the x-ray transmission data to determine a volume of at least one of the pieces of material.

43. The material sorting system of claim 1, wherein the at least one processor is configured to process the x-ray transmission data and x-ray fluorescence data to produce an image from the x-ray transmission data and/or x-ray fluorescence data and to determine x-ray energy attenuation and/or material thickness and/or material shape and size.

44. The material sorting system of claim 1, wherein at least one of the x-ray fluorescence detector array or the x-ray transmission detector is configured as a line scan camera.

45. A method of sorting material, comprising:
conveying one or more pieces of metal with a conveyor;
irradiating the one or more pieces of metal with incident x-rays as they are conveyed by the conveyor to generate fluoresced x-rays from at least a first piece of metal of the one or more pieces of metal and transmitted x-rays transmitted through at least the first piece of metal;
detecting the fluoresced x-rays with an x-ray fluorescence detector array and producing x-ray fluorescence data with the x-ray fluorescence detector array;
detecting the transmitted x-rays with an x-ray transmission detector and producing x-ray transmission data with the x-ray transmission detector; and using at least one processor:
obtaining data for a plurality of characteristic x-ray fluorescence peaks;
identifying a plurality of peaks of the x-ray fluorescence data as corresponding to a respective one of the characteristic x-ray fluorescence peaks;
determining, using the peak identification, the presence of a plurality of materials in the first piece of metal;
obtaining data for a plurality of predetermined sorting categories, at least two of the sorting categories being associated with one or more materials; and
identifying at least one sorting category for the first piece of metal based at least in part on the x-ray transmission data and by comparing the determined plurality of materials in the first piece of metal with the sorting categories.

46. The method of sorting material of claim 45, further comprising:
receiving the x-ray fluorescence data and the x-ray transmission data with the at least one processor;
determining thickness data with the at least one processor for one or more of the one or more pieces of metal based at least in part on the x-ray transmission data; and
combining the thickness data with the x-ray fluorescence data with the at least one processor to determine at least a partial composition of one or more of the one or more pieces of metal.

47. The method of sorting material of claim 46, wherein the x-ray transmission data comprises data about two or more energy levels, and wherein the at least one processor determines the thickness data at least in part by comparing the x-ray transmission data of the two or more energy levels.

48. The method of sorting material of claim 45, wherein the x-ray fluorescence detector array comprises an array of x-ray fluorescence detectors configured to detect fluoresced x-rays from one or more pieces of metal disposed on different parts of the conveyor.

49. The method of sorting material of claim 48, wherein the array of x-ray fluorescence detectors is arranged substantially across a width of the conveyor.

50. The method of sorting material of claim 45, wherein the x-ray transmission detector is a single pixel x-ray transmission detector.

51. The method of sorting material of claim 45, wherein the x-ray fluorescence detector array comprises two rows of x-ray fluorescence detectors.

52. The method of sorting material of claim 45, wherein the conveyor includes one or more openings.

53. The method of sorting material of claim 45, wherein the conveyor comprises one or more mesh sections.

54. The method of sorting material of claim 45, wherein the conveyor comprises two conveyors configured to convey the one or more pieces of metal into and out of an irradiation zone in which the one or more pieces of metal are irradiated with the incident x-rays.

55. The method of sorting material of claim 54, wherein the two conveyors are configured in parallel with a gap between them.

56. The method of sorting material of claim 54, wherein the two conveyors are configured in series.

57. The method of sorting material of claim 45, wherein the conveyor comprises a vibrating feeder.

58. The method of sorting material of claim 45, wherein the x-ray fluorescence data and/or x-ray transmission data form one or more spectra at or about one or more energy levels.

59. The method of sorting material of claim 58, further comprising processing the spectrum with the at least one processor coupled to the x-ray fluorescence detector array.

60. The method of sorting material of claim 59, wherein processing the spectrum comprises performing resultant vector analysis of the spectrum and/or decision tree processing.

61. The method of sorting material of claim 45, wherein the method is used to separate titanium alloys from superalloys.

62. The method of claim 45, wherein the method is configured to separate a first titanium alloy from a second titanium alloy.

63. The method of sorting material of claim 62, wherein the first titanium alloy comprises tin and wherein the second titanium alloy does not.

64. The method of sorting material of claim 45, wherein the method is configured to separate a first superalloy from a second superalloy.

65. The method of sorting material of claim 45, wherein the x-ray fluorescence detector array is configured at approximately 45 degrees from a direction at which the x-ray source irradiates the one or more pieces of metal.

66. The method of sorting material of claim 45, wherein the one or more pieces of metal have thicknesses up to approximately 5 mm.

67. The method of sorting material of claim 45, further comprising selectively ejecting the one or more pieces of metal after they are irradiated with the incident x-rays.

68. The method of sorting material of claim 67, wherein selectively ejecting the one or more pieces of metal comprises using an air ejector.

69. The method of sorting material of claim 67, wherein selectively ejecting the one or more pieces of metal comprises using a paddle ejector.

70. The method of sorting material of claim 45, wherein the x-ray transmission detector and/or x-ray fluorescence detector array comprises one or more detectors selected from the group consisting of: Cadmium Telluride (CdT), Cadmium Zinc Telluride (CZT), lithium drifted silicon (SiLi) and Silicon Drift (SDD) detectors.

71. The method of sorting material of claim 45, further comprising producing an x-ray image of at least one piece of the one or more pieces of metal using the x-ray transmission data.

72. The method of sorting material of claim 45, wherein the method is used to sort the one or more pieces of metal based at least in part on the effective Z (Zeff) of the pieces using the x-ray transmission data.

73. The method of sorting material of claim 45, wherein the one or more pieces of metal comprise alloys and wherein the method is used to sort the alloys.

74. The method of claim 73, wherein the pieces represent machining chips.

75. The method of claim 45, wherein the method is used to remove inclusions of refractory metals from titanium.

76. The method of sorting material of claim 45, wherein the one or more pieces of metal comprise glass, and wherein the method is used to sort the glass.

77. The method of sorting material of claim 45, wherein the one or more pieces of metal comprise mineral ores and wherein the method is used to sort the mineral ores.

78. The method of sorting material of claim 45, wherein the method is fully automated.

79. The method of sorting material of claim 45, further comprising determining a volume of at least one of the one or more pieces of metal using the x-ray transmission data.

80. The method of claim 45, further comprising processing the x-ray transmission data to and/or x-ray fluorescence data to produce an image and to determine x-ray energy attenuation and/or material thickness and/or shape and size of the metal.

81. The method of claim 45, wherein at least one of the x-ray fluorescence detector array or the x-ray transmission detector is configured as a line scan camera.

82. A system, comprising:
a conveyor configured to convey pieces of metal;
an x-ray source configured to irradiate one or more of the pieces of metal while being conveyed by the conveyor;
a multi-channel x-ray fluorescence detector array configured to detect x-rays fluoresced by the one or more pieces of metal, wherein channels of the multi-channel detector array detect x-rays fluoresced from respective parallel regions of the conveyer; and
collimation hardware configured to collimate fluoresced x-rays from the one or more pieces of metal onto the multi-channel x-ray fluorescence detector array by directing to the detector array only fluoresced x-rays that substantially propagate in a first direction.

83. The system of claim 82, wherein the x-ray fluorescence detector array comprises energy dispersive x-ray detectors.

84. The system of claim 83, further comprising a conveyor configured to convey the pieces of metal in two or more parallel channels.

85. The system of claim 82, wherein the multi-channel x-ray fluorescence detector array comprises a plurality of detectors, at least one of which is configured to produce x-ray fluorescence data representing an x-ray fluorescence spectrum.

86. The system of claim 85, wherein each x-ray fluorescence detector of the x-ray fluorescence detector array is configured to produce x-ray fluorescence data representing a respective x-ray fluorescence spectrum.

87. The system of claim 86, further comprising a processor configured to receive the x-ray fluorescence data and concatenate the x-ray fluorescence spectra from the x-ray fluorescence detectors.

88. The system of claim 82, wherein the multi-channel x-ray fluorescence detector array is configured at an angle with respect to a direction at which the x-ray source is configured to irradiate the pieces of metal.

89. The system of claim 82, wherein the one or more pieces of metal are smaller than approximately 20 mm in thickness.

90. The system of claim 82, wherein the multi-channel x-ray fluorescence detector array comprises a linear array of x-ray fluorescence detectors.

91. The system of claim 82, wherein the x-ray fluorescence detector array comprises a 24 pixel line scan camera having a resolution between approximately 0.125 inches and 0.375 inches.

92. The system of claim 82, wherein the x-ray fluorescence detector array comprises a 24 pixel line scan camera having pixels separated by between approximately $\frac{1}{8}$ inch and $\frac{3}{8}$ inch.

93. The system of claim 82, further comprising a processor configured to detect x-ray fluorescence data produced by the x-ray fluorescence detector array and to process the x-ray fluorescence data to identify a chemical composition of individual pieces of metal from the one or more pieces of metal.

94. The system of claim 82, further comprising a channelized gravity-fed slider configured to present the pieces of metal to the x-ray source.

95. The system of claim 82, further comprising an x-ray transmission detector array configured on an opposing side of the one or more pieces of metal from that of the x-ray source.

96. A material sorting system, comprising:
a conveyor configured to convey pieces of metal;
an x-ray source located above the conveyor and configured to irradiate one or more of the pieces of metal with incident x-rays as they are conveyed by the conveyor to generate fluoresced x-rays from the one or more pieces of metal and transmitted x-rays transmitted through the one or more pieces of metal;
an x-ray transmission detector located below the conveyor and configured to detect the transmitted x-rays and produce x-ray transmission data for at least a first piece of metal of the one or more pieces of metal;
a multi-channel x-ray fluorescence detector array located above the conveyor and configured to detect x-rays fluoresced by the pieces of metal and to produce x-ray fluorescence data for at least the first piece of metal, wherein channels of the multi-channel detector array are configured to detect x-rays fluoresced from respective parallel regions of the conveyer; and
at least one processor configured to:
obtain data for a plurality of characteristic x-ray fluorescence peaks;
identify a plurality of peaks of the x-ray fluorescence data as corresponding to respective ones of the characteristic x-ray fluorescence peaks;
analyze the x-ray transmission data to detect an x-ray absorption edge corresponding to at least one element in the first piece of metal;
determine, using the peak identification and the detected absorption edge, the presence of a plurality of alloys in the first piece of metal;
obtain data for a plurality of predetermined sorting categories, each of the sorting categories being associated with one or more alloys; and
identify at least one sorting category for the first piece of metal by comparing the determined plurality of alloys in the first piece of metal with the sorting categories.

97. The material sorting system of claim 96, wherein the first piece of metal comprises tin, and wherein the at least one sorting category identified for the first piece of metal is associated with tin-bearing titanium alloys.

* * * * *